United States Patent
Poupyrev et al.

(10) Patent No.: US 9,341,659 B2
(45) Date of Patent: May 17, 2016

(54) USER INTERACTIVE LIVING ORGANISMS

(71) Applicant: Disney Enterprises, Inc., Burbank, CA (US)

(72) Inventors: Ivan Poupyrev, Pittsburgh, PA (US); Philipp Schoessler, Berlin (DE); Joseph Martin Rohde, Altadena, CA (US); Kathryn Joy Klatt, Pasadena, CA (US); Jeanette Lomboy, Glendale, CA (US); Munehiko Sato, Tokyo (JP); Jason Hintz Llopis, Long Beach, CA (US)

(73) Assignee: Disney Enterprises, Inc., Burbank, CA (US)

( * ) Notice: Subject to any disclaimer, the term of this patent is extended or adjusted under 35 U.S.C. 154(b) by 515 days.

(21) Appl. No.: 13/843,650

(22) Filed: Mar. 15, 2013

(65) Prior Publication Data

US 2013/0221996 A1  Aug. 29, 2013

Related U.S. Application Data

(63) Continuation-in-part of application No. 13/078,028, filed on Apr. 1, 2011, now Pat. No. 8,975,900.

(60) Provisional application No. 61/322,084, filed on Apr. 8, 2010.

(51) Int. Cl.
| | |
|---|---|
| *G01R 27/04* | (2006.01) |
| *G01R 27/32* | (2006.01) |
| *G01R 27/02* | (2006.01) |
| *G06F 3/01* | (2006.01) |

(52) U.S. Cl.
CPC .............. *G01R 27/02* (2013.01); *G06F 3/011* (2013.01); *G06F 3/014* (2013.01)

(58) Field of Classification Search
CPC ...................... G01N 27/02; G01N 2011/0066
USPC ......... 324/633, 300, 334, 655, 658, 675, 708, 324/705
See application file for complete search history.

(56) References Cited

U.S. PATENT DOCUMENTS

| | | | | |
|---|---|---|---|---|
| 4,112,365 | A * | 9/1978 | Larson et al. ................. | 324/173 |
| 5,986,549 | A * | 11/1999 | Teodorescu ................... | 340/561 |
| 6,459,929 | B1 * | 10/2002 | Hopper et al. ................ | 600/513 |
| 6,601,453 | B2 * | 8/2003 | Miyazaki et al. .............. | 73/754 |
| 7,701,338 | B2 * | 4/2010 | Kamizono ........ | B60R 21/01534 307/10.1 |
| 8,026,729 | B2 * | 9/2011 | Kroh .................... | A61B 5/0031 324/633 |
| 8,094,083 | B1 * | 1/2012 | Tam et al. ..................... | 343/788 |
| 8,400,302 | B2 * | 3/2013 | Russell ................ | A61B 5/1038 340/561 |

FOREIGN PATENT DOCUMENTS

JP  58182743  * 10/1983

* cited by examiner

*Primary Examiner* — Tung X Nguyen
*Assistant Examiner* — Giovanni Astacio-Oquendo
(74) *Attorney, Agent, or Firm* — Patterson + Sheridan LLP

(57) ABSTRACT

Embodiments described herein use capacitive sensing to detect human interaction with living plants. A sensing system may utilize the natural conductive paths found in an organic plant to transmit an electrical signal between the plant and a user interacting with the plant. By directly contacting the plant or coming into proximity of the plant, the user may affect the electrical signal. That is, the electrical properties of the user (e.g., the capacitance of the human body) change a measured impedance curve associated with the electrical signal. Based on this change, the sensing system detects an interaction between the user and the plant and may inform a user interaction device to provide a feedback response to the user. For example, the feedback response may be an audio or video effect that is based on the type of user interaction such as whether the user touched the plant's leaf or stem.

17 Claims, 17 Drawing Sheets

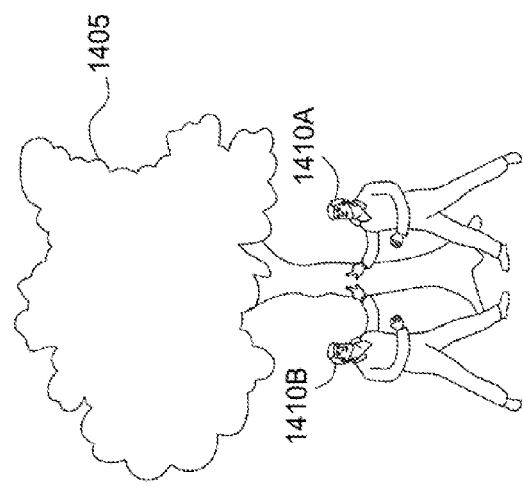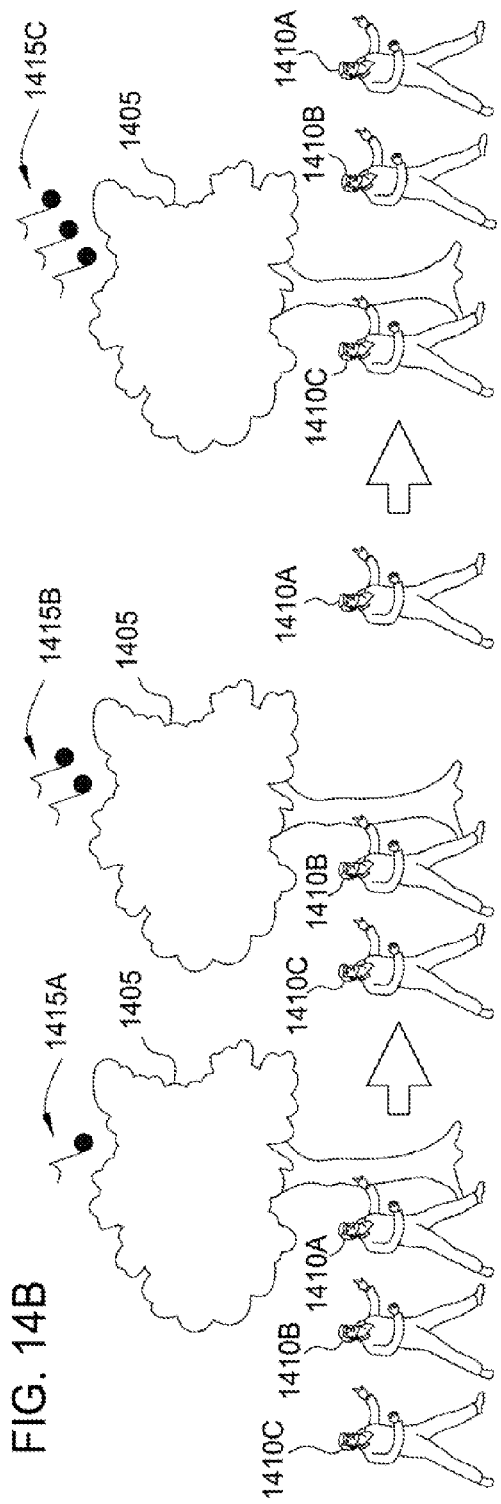

USER INTERACTIVE LIVING ORGANISMS

CROSS-REFERENCE TO RELATED APPLICATIONS

This application is a continuation-in-part of co-pending U.S. patent application Ser. No. 13/078,028 filed on Apr. 11, 2011, entitled "Systems and Methods For Sensing With Resonant Tuning," which claims benefit of U.S. Provisional Patent Application No. 61/322,084, filed on Apr. 8, 2010, entitled "Systems and Methods For Sensing With Resonant Tuning". Each of the aforementioned related patent applications is herein incorporated by reference in its entirety.

BACKGROUND

Research and development in technologies for sensing human activity is at the forefront of an area known as human computer interaction (HCI). The term HCI refers broadly to any interaction between a computing system and a human being, and more particularly, to an interaction in which a human being communicates their intention to a computing system. One way a human being can communicate their intention to a computer system is by having the computer system sense the presence of the human being using a sensor. Examples of such sensors include a proximity sensor and a touch sensor. The desire to sense human activity and communicate human intention to a computer system is leading to the development of new technologies for enabling new types of human-computer interaction. Designing new interactive experiences is one example of a new type of human-computer interaction that exemplifies the need to develop new systems and methods for sensing human activity.

There are a number of different sensing methodologies for detecting the presence and type of human activity and interaction. A sensor is a transducer that converts a physical stimulus, such as light or motion, into a signal that can be measured. The application of the sensor depends on the physical phenomenon sought to be measured, e.g., resistance is measured in resistive touch panels, light intensity is measured in cameras and photo sensors, the direction and intensity of a magnetic field is measured in proximity sensors, acceleration is used to measure motion, and the amount of electrical charge can be used to measure a response of a multi-touch capacitive input device.

When implemented as part of a user interface, one or more sensors can be located in an input device associated with the user interface. The sensor or sensors can be worn by the user or can be embedded into objects and the environment with which the user comes into contact or proximity. Many types of sensors do not have fixed applications and can be used in a variety of applications. One area of HCI research explores using traditional sensor technology in new and creative ways. For example, while a magnetometer is typically used as a sensor for a compass, it can also be used to sense human gestures.

Therefore, it would be desirable to have a sensor that can be used to measure a variety of human actions and activity, such as proximity or touch, deformation and manipulation of objects and other actions that can be used to sense the presence and intention of a human being and that can be used as part of a user interface for a computer system.

SUMMARY

One embodiment of the present disclosure is a method. The method includes transmitting an alternating current (AC) signal at two different frequencies in an organic plant. The method includes detecting a change in a parameter based on measuring impedance values at the two different frequencies where the changed parameter is caused by a subject becoming electrically coupled to the organic plant. The method also includes identifying an action performed by the subject based on the changed parameter and providing a feedback response to the subject based on the identified action.

Another embodiment of the present disclosure is a system that includes an organic plant. The system also includes a sensing component configured to transmit an alternating current (AC) signal at two different frequencies in the organic plant and detect a change in a parameter based on measuring impedance values at the two different frequencies, where the changed parameter is caused by a subject becoming electrically coupled to the organic plant. The changed parameter is used to identify an action performed by the subject. The system also includes a user interaction device communicatively coupled to the sensing system, the user interaction device configured to provide feedback response to the subject based on the identified action.

Another embodiment of the present disclosure is a system for sensing human activity by monitoring impedance. The system includes a signal generator for generating an alternating current (AC) signal, the AC signal applied to an organic plant and a subject electrically coupled to the AC signal in the organic plant. The system also includes an envelope generator for converting a returned AC signal to a time-varying direct current (DC) signal. The system includes an analog-to-digital converter for determining a defined impedance parameter of the time-varying DC signal, where the defined impedance parameter defines an electromagnetic resonant attribute of the organic plant.

BRIEF DESCRIPTION OF THE DRAWINGS

So that the manner in which the above recited aspects are attained and can be understood in detail, a more particular description of embodiments of the invention, briefly summarized above, may be had by reference to the appended drawings.

It is to be noted, however, that the appended drawings illustrate only typical embodiments of this invention and are therefore not to be considered limiting of its scope, for the invention may admit to other equally effective embodiments.

FIGS. 14A and 14B illustrate providing interactive feedback based on multiple individuals interacting with the same living plant, according to embodiments described herein.

DETAILED DESCRIPTION

Figure 1:
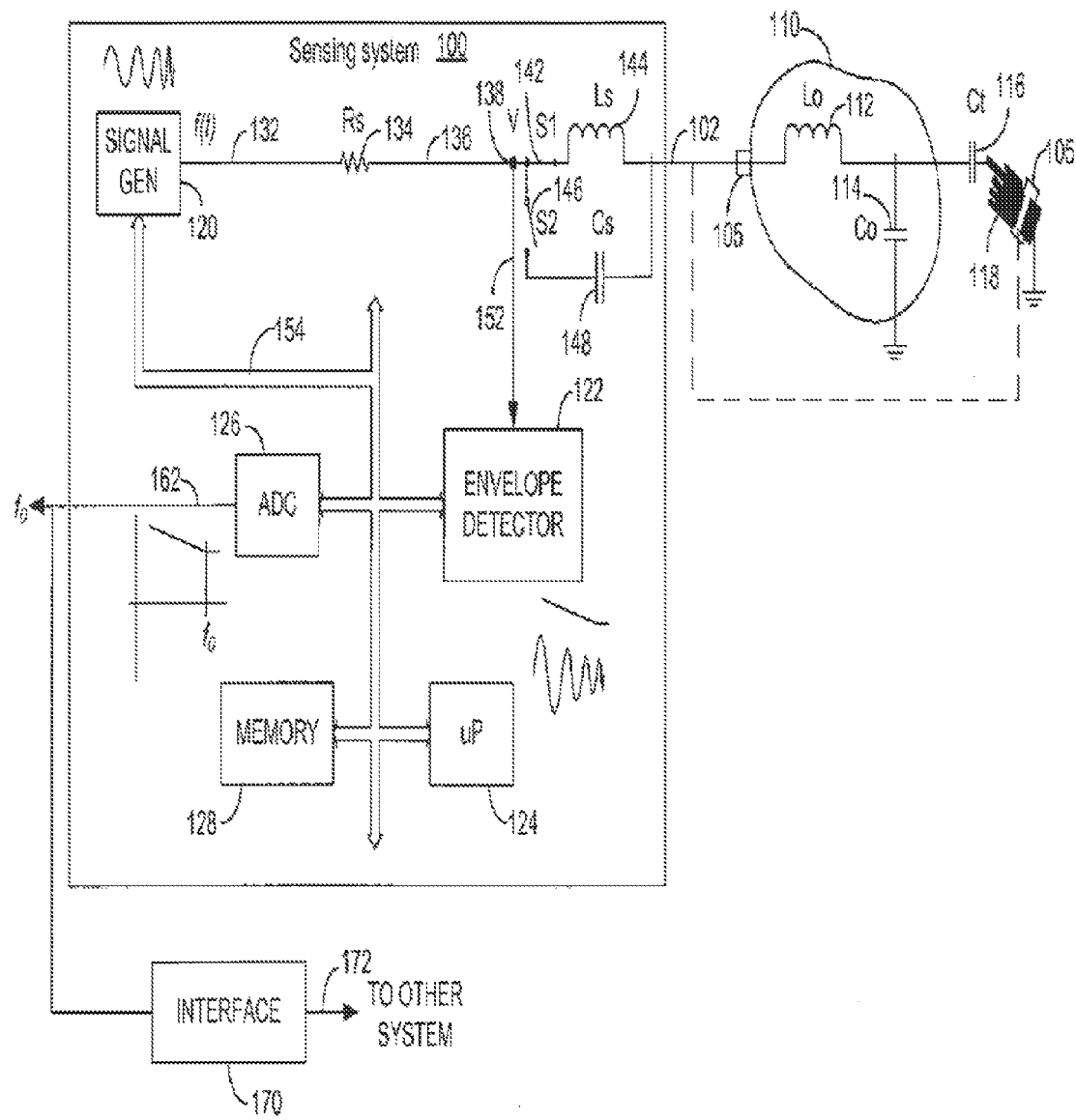
FIG. 1 is a block diagram illustrating an embodiment of a system for sensing human activity by monitoring impedance.

The system and method for sensing human activity by monitoring impedance is based on a physical phenomenon known as impedance. Impedance is generally defined as the total opposition a device or circuit offers to the flow of an alternating current (AC) at a given frequency and includes phase and amplitude components. For many objects, the frequency at which the opposition to the flow of alternating current drops to its minimum is referred to as the object's resonant frequency. Resonant frequency is related to the effect of the electromagnetic resonance of an object. For some objects, the value of the impedance is minimal at the object's resonance frequency and for other objects the value of the impedance is maximal at the object's resonant frequency. Electromagnetic resonance has been widely used for tuning and filtering radio communication circuits, as well as for identifying and tagging objects. These uses assume that the resonant characteristics of the object are known ahead of time, whereby the user manipulates a specific tag or identification card. However, any system of conductive objects, including humans, has resonant properties that can be described by defined impedance parameters, such as resonant frequency, or other parameters. For these reasons, the electromagnetic resonance, and in particular, resonant frequency, can be used as an indicator for sensing human activity. Assuming that the electrical properties of the object or system are constant, any changes in the resonant properties of the object or system result from user activity or user interaction. Therefore, human interaction with the object or system can be detected by a) measuring the impedance of the system at various frequencies and generating what are referred to as "impedance curves" that are representative of the system's impedance over a range of frequencies, b) computing various resonant properties and other features from the impedance curves, and c) monitoring changes in the computed resonant properties of the object or system at different frequencies. Resonant properties include the resonant frequency of the object or system as well as other resonant properties, such as an amplitude of a measured signal at the resonant frequency, the profile of the peaks of the measured signal, as well as the presence of other peaks in an impedance curve.

Changes in the resonant properties of the object or system arise due to direct or indirect interaction between a user and the object or system. For example, by measuring changes in the resonant frequency of an object when a user interacts with the object, the type and extent of the interaction can be identified. The remainder of this description will generally focus on monitoring changes in the resonant frequency and other related impedance parameters of an object or system to determine the type of and extent of human interaction with the object or system. As used herein, the terms object and system will be used interchangeably to refer to an object or system, the impedance, and in an embodiment, the resonant frequency of which is sought to be measured and monitored to determine human interaction with the object or system.

Any electrical system with capacitive, inductive and resistive elements has a unique frequency at which an alternating current flowing through the system will reach a maximum or a minimum value, i.e., its resonant frequency. The maximum and minimum values could also take the form of local minimum and local maximum values. While many systems correspond to a minimum alternating current value at their resonant frequency, there are some systems that correspond to a maximum alternating current value at their resonant frequency. Both instances are contemplated herein, depending on the system. The system can be stimulated by applying a periodic electrical signal over a range of different frequencies, e.g. by performing a frequency sweep of the system. The amplitude of the alternating current reaches its minimum or maximum at the resonant frequency of the system, and can therefore be used as an indicator of the resonant frequency of the system.

Any interaction that affects the reactive properties of the system (i.e. capacitance or inductance) will change the impedance characteristics, and in an embodiment, the resonant frequency of the system. Assuming the electrical properties of the system remain constant, any changes in the resonant frequency will occur due to human activity or interaction with the system. Thus, it is possible to infer human interaction with the system by tracking changes in the resonant frequency of the system.

The resonant frequency of a circuit that includes capacitive, inductive and resistive properties can be generally described by Equation 1.

$$f_0 = \frac{1}{2\pi\sqrt{L \cdot C}} \quad \text{Eq. 1}$$

where L is the inductance in C is the capacitance of the system. The resonant frequency of the system changes only when the system's inductance and capacitance are affected.

Capacitive interactions change the capacitive properties of the system. For example, a user touching a conductive object, such as a metal bracelet worn on a user's wrist, forms a capacitive link to ground, increasing capacitance and decreasing the resonant frequency of the bracelet. Another example of capacitive interaction is the physical reconfiguration of the object such as opening or closing a drawer in a metal cabinet. Such reconfiguration leads to changes in system capacitance and changes in the resonant frequency.

Inductive interactions change the inductive properties of the system. For example, stretching a metal spring will change its inductance, as the inductance depends on the distance between the turns of the spring. Changing the inductance changes the resonant frequency of the system. Accordingly, a sensor configured to determine the resonant frequency of an object or system should be sensitive to changes in the capacitance and inductance of the object or system.

FIG. 1 is a block diagram illustrating an embodiment of a system for sensing human activity by monitoring resonant frequency. The sensing system 100 is coupled to an object 110 over connection 102. In an embodiment, the connection 102 can be a single wire. An electrode 105 can be attached to the object 110, or can be attached to a human 118, depending on the application.

The object 110 can be any conductive object or system that has electromagnetic resonant properties and, in an embodiment, a resonant frequency characterized by an inductance (Lo) 112 and a capacitance (Co) 114. The inductance (Lo) 112 and the capacitance (Co) 114 can be known or unknown. The inductance (Lo) and the capacitance (Co) correspond to the inductance, L, and the capacitance, C, in Equation 1. To illustrate human interaction, a human 118 touches the object 110, in which the touch illustrates a capacitive contact between the human 118 and the object 110. The capacitance, Ct, 116 illustrates that the touch causes a change in the overall capacitive reactance of the object 110. A particular configuration of inductive and capacitive elements in the object 110 are provided as an example. In general the exact configuration may not be known and can be arbitrary and complex. However, the operation of the systems and methods described herein are not dependent on knowledge of the exact configuration of the inductive and capacitive elements in the object 110.

The sensing system 100 comprises a signal generator 120, an envelope detector 122, a microprocessor 124, an analog to digital converter 126, and a memory 128, coupled over a system bus 154. The system bus 154 can be any communications bus that allows interoperability and communication between and among the connected elements. The microprocessor 124 can be any general purpose or special-purpose processor that can execute the functions described herein. The memory 128 can be any type of static or dynamic memory, volatile or non-volatile memory, and can, in an embodiment, be used to store software related to the operation of the systems and methods described herein. The memory 128 can be either or both of local memory and/or memory located on other computing devices and that is accessible using various data transmission technologies, such as wired or wireless connection links. The memory is also used to store the results provided by the sensing system 100.

The signal generator 120 generates a time varying signal f(t), which is provided over connection 132. In an embodiment, the signal provided over connection 132 is a 1 KHz to 3.5 MHz, 10V peak-to-peak, sinusoidal frequency sweep, which is provided to a resistor 134. The resistor, Rs, 134 has a relatively small value and converts the alternating current on connection 132 to an alternating voltage on connection 136. The alternating voltage on connection 136 is provided through a node 138 to a first switch 142 and to a second switch 146. The switches 142 and 146 can be controlled manually, by the microprocessor 124 or by any circuitry that can be specific to the embodiments described. The first switch 142 is connected to a biasing inductor, Ls, 144, and the second switch 146 is connected to a biasing capacitor, Cs, 148. The switches 142 and 146 can be selectively opened and closed by the microprocessor 124, or by other logic or circuitry. For most objects, the capacitance, Co, 114 and the inductance, Lo, 112 are very small, resulting in a very high resonant frequency.

Both capacitive and inductive interactions with the object 110 affect the form of the impedance curve, as well as the width of local or global peaks in the impedance curve corresponding to resonant frequency i.e., its Q-factor, with a resultant change in the resonant frequency of the object 110, or a change in other parameters To infer human interaction with the object 110 from changes in a measurable parameter, a correspondence between human interaction and the affected parameter should be established. Therefore, it could be preferable in some applications to block the effect of either capacitive or inductive interactions. Doing so ensures that changes in the resonant frequency, or Q-factor, are the result of changes in one, but not both types of interactions. For example, if it is desirable to measure the stretching of twisted wire, i.e. an inductive interaction, it would be desirable to remove the influence of the user touching the wire, which is a capacitive interaction and which would also affect the measurement of the resonant frequency.

Blocking the influence of inductive interactions can be accomplished by adding the biasing inductor, Ls, 144, and blocking the influence of capacitive interactions can be accomplished by adding the biasing capacitor, Cs, 148. In addition to blocking the influence of inductive and capacitive interactions, selectively introducing the biasing inductor, Ls, 144 and the biasing capacitor, Cs, 148 between the connection 136 and the connection 102 also shifts the resonant frequency of the entire system including the sensing system 100 and object 110 into a lower range that is more easily measured than a very high resonant frequency. For example, if it is desired to track capacitance changes in the system 110, a large value for the biasing inductor, Ls, 144 not only blocks the influence of inductive changes in the object 110, but also shifts the resonant frequency into a lower, more easily measurable range. Similarly, if it is desirable to track inductive changes in the object 110, a large biasing capacitor, Cs, 148 is switched into the system, thus blocking the influence of capacitive changes in the object 110 and shifting the resonant frequency into a lower, more easily measurable range. Generally, either the biasing inductor, Ls, 144 or the biasing capacitor, Cs, 148 will be connected to node 138 at a given time. The biasing inductor, Ls, 144 and the biasing capacitor, Cs, 148 can be referred to as reactance altering elements because they influence the AC voltage on node 138.

The large biasing inductor, Ls, 144 blocks inductive effects imparted to the object 110, thus enabling the measurement of small changes in capacitance. A large biasing capacitor, Cs, 148, blocks capacitive effects, thus enabling the measurement of small changes in inductance of the object 110.

In an embodiment, the alternating voltage at node 138 characterizes the resonant frequency of the object 110, including the effect imparted by the biasing inductor, Ls, 144 or the biasing capacitor, Cs, 148. The alternating voltage at node 138 is provided to an envelope detector 122. The envelope detector 122 generates a time varying DC signal that defines the amplitude of the alternating voltage at node 138. The signal on connection 152 represents a signal returned from the object 110. The time varying DC signal is provided to the analog to digital converter (ADC) 126. The analog to digital converter 126 processes the time varying DC signal provided by the envelope detector 122 to determine a local minimum, a local maximum, or other attribute of the measured signal. In an embodiment, the local minimum of the time varying DC signal corresponds to the resonant frequency, $f_0$, of the object 110. The signal representing the resonant frequency, $f_0$, is provided over connection 162 to systems external to the sensing system 100. In an embodiment, the signal, $f_0$, is provided to an interface 170. The interface 170 can be any interface that can use the information about the resonant frequency of the object 110. For example, the interface 170 can be a user interface that provides an input/output function to a computing device, a portable communication device, an interactive toy, a sensing system associated with an attraction at an amusement park, or any other computer-based interface. The output of the interface on connection 172 is shown as being provided to another system to signify that the output of the sensing system 100 can be used by a number of different systems in a number of different configurations.

The ability to accurately measure the resonant frequency of an object 110 with very small capacitance and inductance allows the resonant frequency of the object to be identified and tagged, thereby providing the ability to recognize the object 110 based on its resonant frequency. For example, the resonant frequency of the object 110 can be measured and stored in the memory 128 so that at a later time, the resonant frequency can be used to identify that object 110.

Figure 2A:
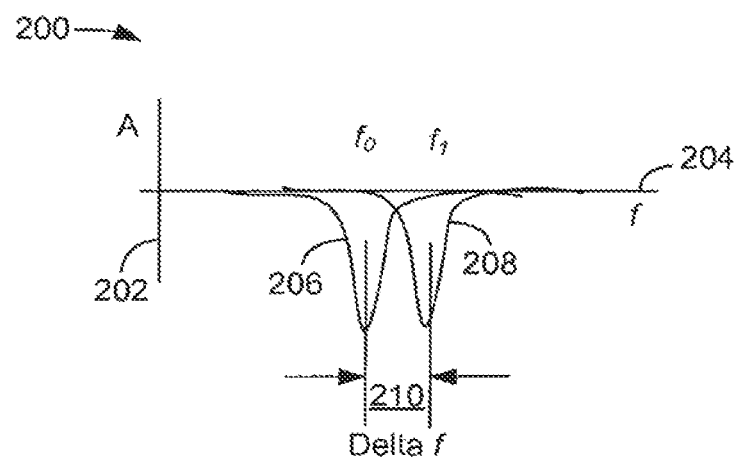
FIG. 2A is a graphical view illustrating an example of a measurable change in the resonant frequency of an object due to human interaction.

FIG. 2A is a graphical illustration 200 of an example of a measurable change in the resonant frequency of an object due to human interaction. The vertical axis 202 represents amplitude of a measured signal and the horizontal axis 204 represents frequency. A first resonant frequency trace 206 illustrates a measured signal that has a first resonant frequency $f_0$. A second resonant frequency trace 208 illustrates a measured signal that has a second resonant frequency, referred to as f1. In an embodiment, the resonant frequency, $f_0$, can be the static resonant frequency of the object 110. The second resonant frequency, $f_1$, represents the resonant frequency of the object 110 while being touched by a human being 118. As shown in FIG. 2A, the change in the resonant frequency, referred to as $\Delta f$, 210, shows the effect of a human being interacting with the object 110 by touching the object 110. For example, if the object 110 is a wristwatch bracelet that is connected to the sensing system 100 with an electrode 105 over connection 102, the effect of a human being 118 touching the object 110 results in a change in the resonant frequency of the object by an amount shown in FIG. 2A as $\Delta f$. The ability of the sensing system 100 to measure this change in resonant frequency allows the sensing system 100 to be used as a user interface, or as part of a user interface that can communicate human interaction with the object 110 to other computing devices and computing systems.

Figure 2B:
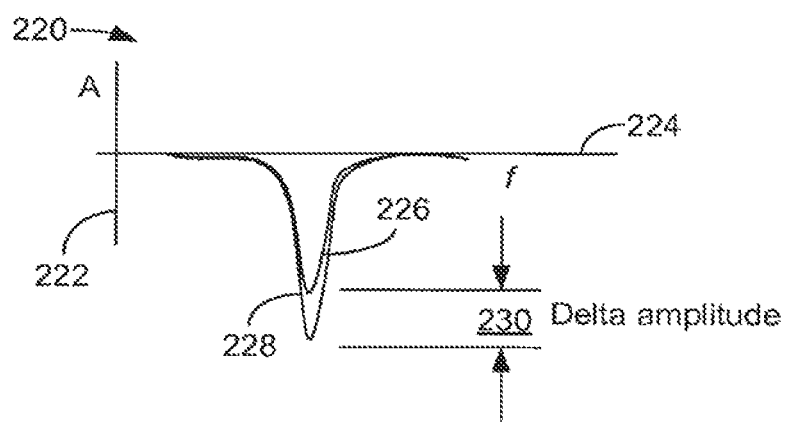
FIG. 2B is a graphical view illustrating an alternative measurable parameter of the object of FIG. 1.

FIG. 2B is a graphical view illustrating an alternative measurable parameter of the object of FIG. 1 that can be measured by the sensing system 100. The vertical axis 222 represents amplitude and the horizontal axis 224 represents frequency. A first resonant frequency trace 226 illustrates a measured signal that has a first resonant frequency $f_0$. A second resonant frequency trace 228 illustrates a measured signal that has a second resonant frequency, referred to as $f_1$. In this example, the first resonant frequency $f_0$ is substantially similar to the second resonant frequency $f_1$. In an embodiment, the resonant frequency, $f_0$, can be the static resonant frequency of the object 110. The second resonant frequency, $f_1$, represents the resonant frequency of the object 110 while being touched by a human being 118.

In FIG. 2B, a change in the amplitude from the first resonant frequency trace 226 to the second resonant frequency trace 228, referred to as $\Delta$amplitude 230 results from human interaction with the object 110. In this embodiment, amplitude is the defined impedance parameter and the amplitude difference, $\Delta$amplitude 230, can be measured by the ADC 126 and used to signify human interaction with the object 110. Further, a combination of frequency and amplitude can be measured and used to signify human interaction with the object 110.

Figure 3:
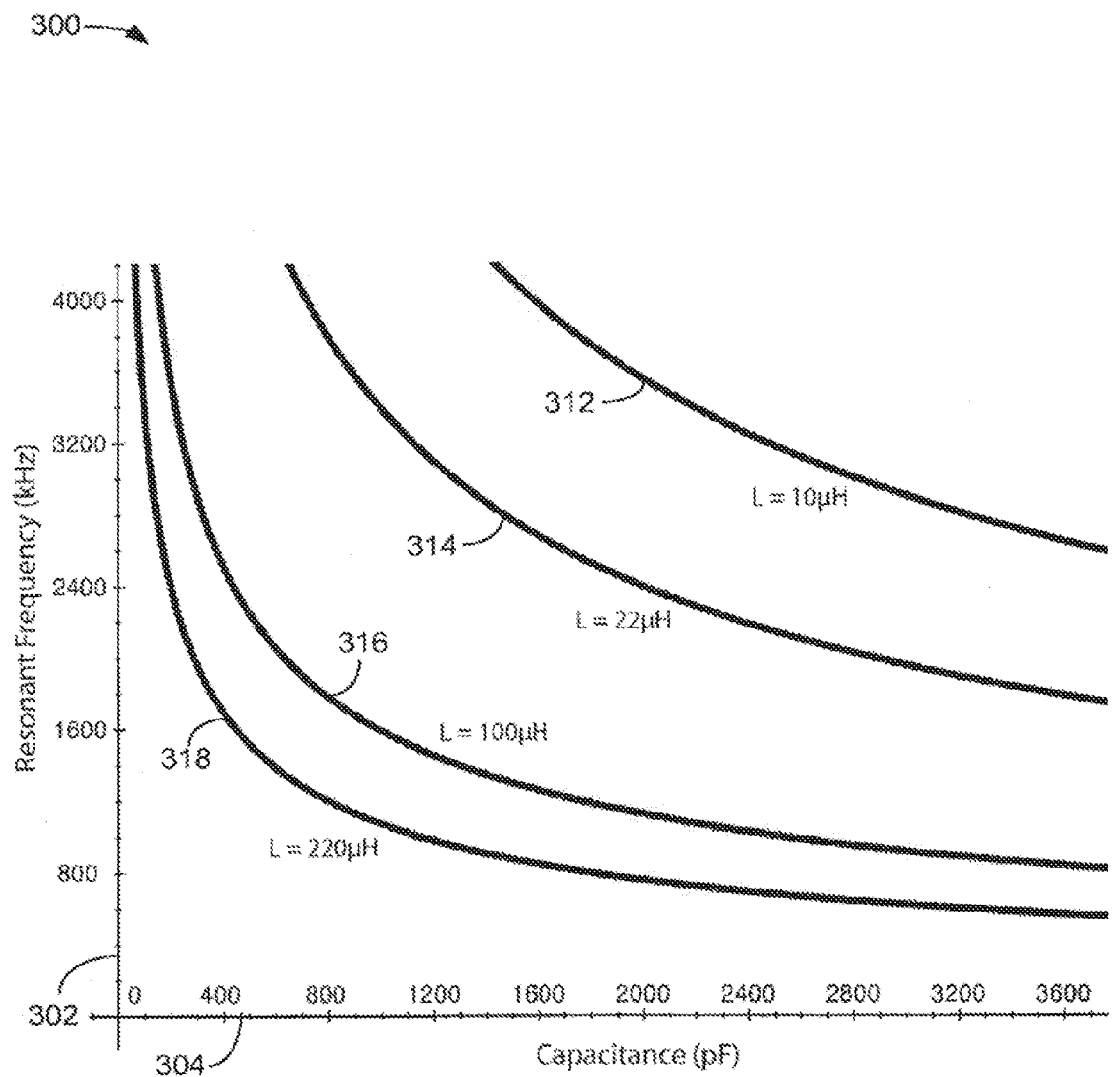
FIG. 3 is a graphical illustration showing the effect of a biasing inductor on the capacitance and resonant frequency of an object.

FIG. 3 is a graphical illustration 300 showing the effect of a biasing inductor on the capacitance and resonant frequency of an object. The vertical axis 302 represents resonant frequency in kHz and the horizontal axis 304 represents capacitance in pF. The traces 312, 314, 316 and 318 respectively show the effect of biasing inductance, Ls, 144 (FIG. 1) values of 10 µH, 22 µH, 100 µH and 220 µH. As inductance increases, the resonant frequency becomes more sensitive to small variations in capacitance in lower range of values as the resonant frequency drops. Therefore, small variations in capacitance can be measured at very small values while remaining in a lower range of resonant frequencies. At the same time it can be observed that as the value of inductance increases, the system becomes less sensitive to small changes in total inductance. Therefore, by including a large biasing inductor, the effect and influence of inductance can be effectively blocked. Blocking the inductance will ensure that changes in the resonant frequency can be measured by small capacitive interaction only. Alternatively, a large biasing capacitor can be used to block the influence of capacitance changes and allow the measurement of resonant frequency as a result of small changes in inductance.

Figure 4A:
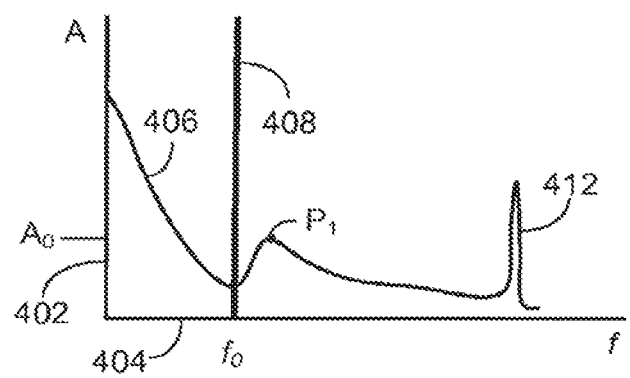
FIG. 4A is a graphical illustration showing an exemplary plot of the static resonant frequency of an object.

FIG. 4A is a graphical illustration 400 showing an exemplary plot of the static impedance of an object. The vertical axis 402 represents amplitude and the horizontal axis 404 represents frequency. The trace 406 illustrates a plot of the static impedance curve of the object 110. The term "static" impedance refers to the impedance of the object 110 with no human interaction. The trace 406 shows the static impedance curve of the object 110 over a range of different frequencies. The resonant frequency, $f_0$, is illustrated at 408. The resonant frequency 408 can be stored in the memory 128 and can be associated with the object 110. Associating the resonant frequency 408 with the object 110 allows the identity of the object 110 to be saved and used at a subsequent time to identify the object 110.

Figure 4B:
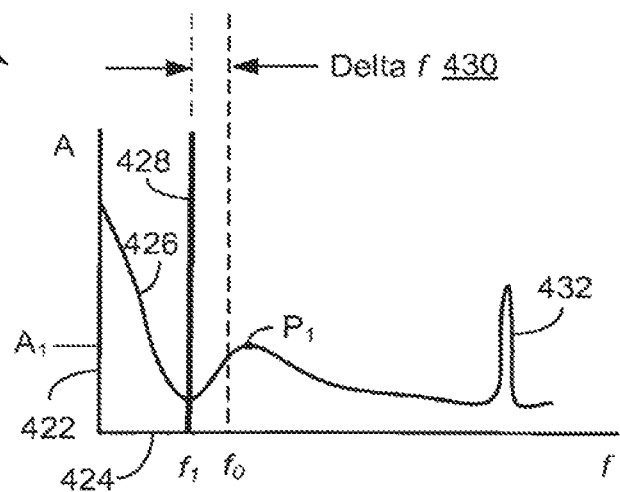
FIG. 4B is a graphical illustration showing an exemplary plot of the resonant frequency of the object of FIG. 4A after human interaction.

FIG. 4B is a graphical illustration 420 showing an exemplary plot of the impedance of the object of FIG. 4B during human interaction. The vertical axis 422 represents amplitude and the horizontal axis 424 represents frequency. The trace 426 illustrates a plot of the impedance curve of the object 110 during human interaction. The trace 426 shows the impedance curve of the object 110 over a spectrum of different frequencies and reflects changes in the static impedance curve of FIG. 4A shown by trace 406. The change in the impedance curve shown in trace 426 reflects changes in one or more impedance parameters of the object 110 resulting from human interaction. These changes result in a change in, for example, the resonant frequency, which changes from a value $f_0$ in FIG. 4A to a value of $f_1$ in FIG. 4B. Changes in other impedance parameters, such as amplitude, a combination of resonant frequency and amplitude, or other impedance parameters can also be monitored for change which can signify human interaction with the object 110. Other features of the impedance curve, such as differences in the amplitude, shape and width of a peak 412 (FIG. 4A) and a corresponding peak 432 (FIG. 4B), can be monitored for change, which can also signify human interaction.

As an example of human interaction with the object 110, when a user touches the object 110 with their finger, the user's finger creates a variable capacitance with the object. The capacitance can vary with the amount of pressure exerted by the user's finger on the object. As the user presses harder, the skin stretches and increases the area of touch, thereby increasing the capacitance, and thereby altering the trace 426. The resonant frequency, is the resonant frequency of the object 110 in response to the human interaction and is illustrated at 428. The difference in resonant frequency, $\Delta f$, 430, reflects the difference in resonant frequency between $f_0$ and is indicative of the human interaction with the object 110. The value of $f_0$, $f_1$ and $\Delta f$ can be stored in the memory 128 and used to identify the object 110 and the type of interaction with the object 110. In addition to the frequency, other parameters, such as, for example, the amplitude of the trace at a particular frequency can also be monitored for change that can signify human interaction. For example, a point, $P1$, on the trace 406 in FIG. 4A might occur at an amplitude, $A_0$. The point $P1$ may exhibit a change in amplitude, shown as $A_1$ in FIG. 4B, to signify human interaction, and further, to signify a degree of human interaction.

Figure 5:
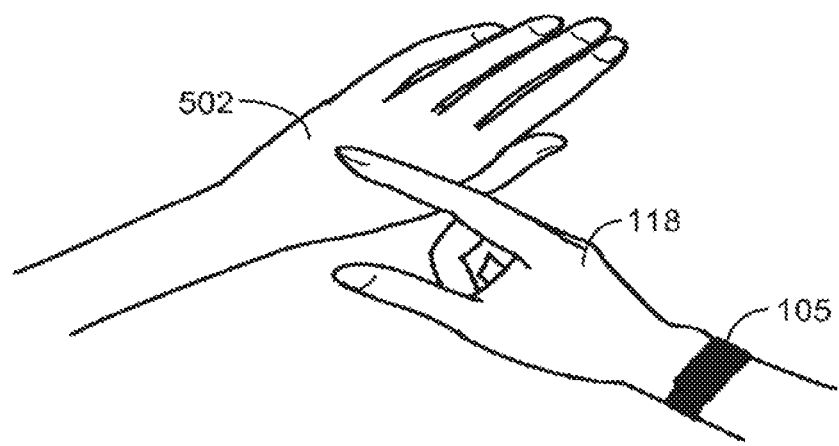
FIG. 5 is a schematic diagram illustrating a first example of a manner in which the system for sensing human activity by monitoring impedance can be used.

FIG. 5 is a schematic diagram illustrating a first example of a manner in which the system for sensing human activity by monitoring impedance can be used. The electrode 105 is attached to the user's body 118, such as to a finger or wrist. The sensing system 100 records changes of the parameters describing the impedance curve (FIGS. 4A and 4B) as the user touches various objects in the environment or changes their relation to the environment. In FIG. 5, the user 118 is touching their own body, such as another arm, fingers or a cheek, or in this example, their hand 502. The change in the measured impedance parameter or parameters depends on, for example, the extent to which the user 118 touches their own body, e.g. the area of contact and the force of contact. The measured impedance parameters can determine, for example, whether the user touches them self with one finger, with two fingers or with three fingers. The measured impedance parameters can also be used to determine how much pressure the user applies. The measured impedance parameters can be then mapped to correspond to various interaction actions. For example, tapping ones hand with one finger could start playback of a digital music player, while tapping ones hand with two fingers could stop playback of the digital music player. Other media devices, game devices, communication devices, appliances, etc., and their related functionality can be controlled in similar manner.

In another example, one or more of the parameters of a music synthesis device could be controlled by the user squeezing their own arm, where squeezing the arm stronger, for example, could increase the pitch of the sound. In another example, an external system can be controlled by clapping, where the sensing system 100 can recognize the extent to which the clapping hand is touching the other hand, e.g. if it is touching only with the tips of the finger or with the entire palm. This measured impedance characteristic can be then applied to control the device.

In another example the user 118 can distinguish which parts of their own body the user is touching, either by equipping the body with additional electrodes or by recognizing that different body parts have different electrical properties.

In other examples, the user may raise one or both feet from the ground. The change in measured impedance parameters could describe how much the user 118 raises their feet from the ground, as well as if the user raises one foot or both feet.

The measured impedance parameters can be used to measure user state and can be saved to memory 128 (FIG. 1) and mapped to control at least some of the parameters of the interaction. For example, comparing the measured impedance parameters can determine whether the user is touching the ground with his feet, which allows the measurement of the number of steps the user has taken and other properties of locomotion. For example, comparing the measured impedance parameters can distinguish between running and walking.

The system and method for sensing human activity by monitoring impedance can also be used to distinguish different objects that the user may be touching or with which the user may be in proximity. Different objects could affect parameters of the impedance curves differently when the user touches them. Based on the measured impedance parameters, it is possible to distinguish how and to what extent the user is touching the object, e.g. how hard the user is touching the object, how many fingers are touching the object and so on. This is possible because the larger the area of contact with the object, the more pronounced will be the change in the measured impedance parameters. The sensing system 100 can distinguish between the objects that the user is touching as follows. For one or more objects, when the user touches an object the sensing system 100 records the measured impedance parameters of the impedance curve and stores the measured impedance parameters in the local memory 128 (FIG. 1). Subsequently, if the user 118 touches the same object, the sensing system 100 compares the subsequently measured impedance parameters with those stored in the memory 128 and if a match is found, identifies the object 110. There are a number of ways this can be accomplished. The object can be distinguished without any instrumentation, by measuring impedance parameters of the impedance curve (426, FIG. 4B). Alternatively, the object 110 can be instrumented with additional passive components (e.g. capacitors and inductors) to create a unique "signature" that would allow the sensing system 100 to distinguish which object the user is touching. If the object consists of different parts, such as individual drawers, doors, legs, etc, the sensing system 100 can distinguish which part the user is touching. In another example, the other object can be a person. For example, shaking hands can result in a unique impedance curve and have a unique measured impedance parameter. Further, the measured impedance parameter can reflect differences depending on how many people are touching each other. Therefore, the sensing system 100 can distinguish when several people are joining hands and form a larger configuration of people.

It is also possible to track an object inside of the user's body. The measured impedance parameter of the impedance curve changes when the user is changing the properties of the body. For example, if an electrode 105 is attached to a user's cheek, the sensing system 100 can track when the user 118 moves water inside of their mouth.

Figure 6:
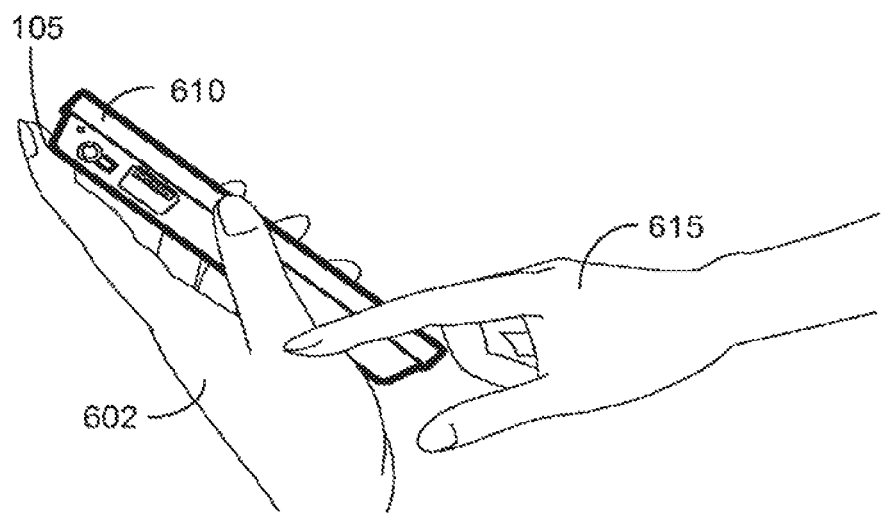
FIG. 6 is a schematic diagram illustrating a second example of a manner in which the system for sensing human activity by monitoring impedance can be used.

FIG. 6 is a schematic diagram illustrating a second example of a manner in which the system for sensing human activity by monitoring impedance can be used. In the example shown in FIG. 6, the user 118 does not wear the electrode 105 on their body, but instead holds a mobile device 610 in their hand 602. In this example, the mobile device is a mobile phone. The mobile device 610 has an electrode 105 embedded in its case. An advantage of this configuration is that the user does not have to wear anything. The interaction starts naturally when the user 118 picks up the mobile device 610. Another advantage is that the effects of the interaction are defined and encapsulated by the mobile device 610, i.e. a different device would have different effects. For example if the user 118 holds a mobile device 610 and touches their holding hand 602 with another hand 615, then a call can be put on hold. However, if the device is a gaming device, performing the same actions could result in a game related action, such as shooting or flying. Other applications can also be designed.

Figure 7A:
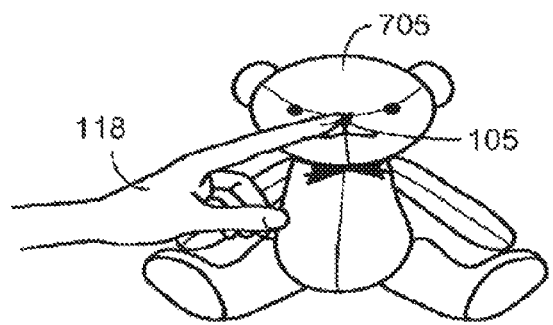
FIGS. 7A and 7B are schematic diagrams collectively illustrating another example of a manner in which the system for sensing human activity by monitoring impedance can be used.
Figure 7B:
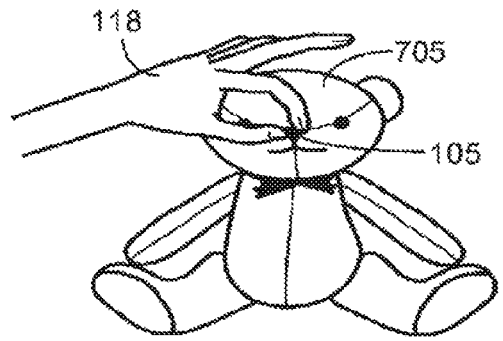

FIGS. 7A and 7B are schematic diagrams collectively illustrating another example of a manner in which the system for sensing human activity by monitoring impedance can be used. The sensing system 100 can recognize properties of touch when a user 118 is touching the electrode 105. For example if the object is an interactive toy 705, the sensing system 100 can recognize the user 118 touching the object as well as how strongly the user is touching the object, such as using a single finger in FIG. 7A and using two fingers in FIG. 7B, and then cause an interface (170, FIG. 1) associated with the sensing system 100 to react in a manner appropriate to the touch.

The electrode 105 can be attached to a non-conductive object, which, in an embodiment, can be used as a handle for the electrode 105. For example the electrode 105 can be attached to the end of the wooden stick that is used like a magic wand. The handle of the non-conductive object therefore can be manipulated by the user in a way that the internal state of the user does not affect the sensing system 100. Advantages of this arrangement include there being a much clearer and direct connection between the electrode 105 and the objects in the environments that the user is interacting with, as opposed to the case where the electrode is attached to the user's hand. Furthermore, the internal state of the user 118 would not affect the measured signal because the user 118 and the sensing system 100 are separated.

The sensor 105 can also be attached to a conductive object located in the environment. The sensing system 100 recognizes individuals who are touching the object by analyzing the measured impedance parameters that can be associated with a particular individual. The sensing system 100 can distinguish between people of different sizes, e.g. large body and small body. The sensing system 100 can distinguish between children and adults. For example an attraction in an amusement park can behave differently depending on whether a child or an adult interacts with the attraction.

The sensing system 100 also can distinguish between humans and non-humans, or between humans and multiple humans. For example, the sensing system 100 can be used to accurately track the presence of humans in ride vehicles in an amusement park.

When implemented as a stylus used as an input device, the stylus can be instrumented with one or more electrodes and/or sensing systems and change the properties of an interface depending on how the user is interacting with the stylus. For example, a light touch on the stylus could create a thin line and strong touch on the stylus could create a thick line.

In another example, a computer input device can track the proximity of a touching finger and then clearly distinguish between touch and proximity of the user to the object.

The object can become interactive in an adhoc manner, i.e. an object 110 was not interactive before but becomes responsive to user interaction after the sensing system 100 is attached to it. For example, a refrigerator could become interactive when the sensing system 100 and electrode 105 are attached to it.

In another example, an electrode 105 can be placed into water or other conductive liquid and then one or more parameters of the liquid can be measured by monitoring a change in the measured impedance parameter. The sensing system 100 system could also respond depending on how much of the object 110 is placed into the water, e.g. a partially submerged object would produce a different reaction from completely submerged object. An amount of liquid flowing through an object, such as a pipe, can also be measured. Interaction with running liquid can also be measured.

Changes in the internal state of the object 110 can also be measured. These changes can be caused by the user 118 as they interact with the object 110, environment or internal changes in the object 110.

In another example, the electrode 105 can be attached to an object 110 and the object 110 can "sense" changes in its configuration. For example, a refrigerator can recognize when the door is open or closed, or a cabinet can be instrumented to recognize when a specific drawer is open.

In another example, the sensing system 100 can measure the wear of an object 110 as the user 118 interacts with it. For example, the sensing system 100 can be attached to the graphite core of a pencil and a conductive plane can be placed underneath the paper. The sensing system 100 can measure the exact area of touch of the pencil tip on the paper and as the user sketches and the tip of the pencil wears, the area of pen touching paper can be continually tracked. This information can be mapped into the thickness and other properties of lines that are being drawn on the paper.

The sensing system 100 can measure the growth of an object 110 such as a plant. The sensing system 100 can also measure how the configuration of the plant changes with time or how the internal state of the plant changes with time.

Figure 8A:
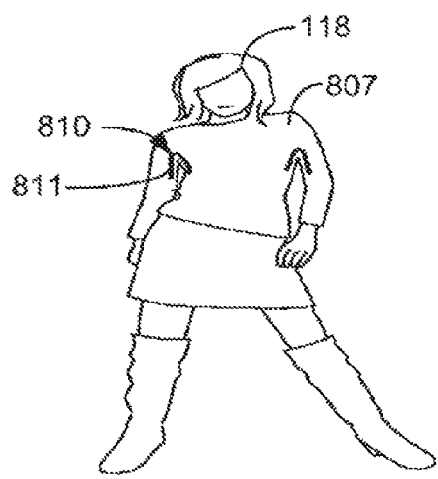
FIGS. 8A and 8B are schematic diagrams collectively illustrating another example of a manner in which the system for sensing human activity by monitoring impedance can be used.
Figure 8B:
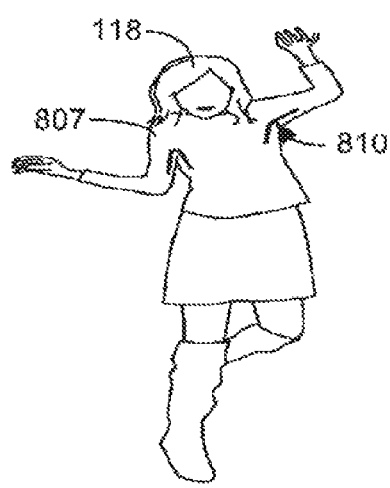

FIGS. 8A and 8B are schematic diagrams collectively illustrating another example of a manner in which the system for sensing human activity by monitoring impedance can be used. The electrode 105 can be attached to a stretchable object 810 and can be used to measure the amount that the object 810 stretches. Stretching is an inductive interaction. In this example, it is desirable to estimate the changes in the inductive properties of the object 810. In an example, the object 810 is a flexible coil and the sensing system 100 can measure how far the user 118 is stretching the flexible coil. As an example, the flexible coil can be a conductive thread 811 that is woven into fabric 807 of a garment worn by the user 118. As the fabric 807 stretches, the conductive thread 811 also stretches. The amount that the conductive thread 811 stretches can be indicated by analyzing the measured inductive parameters that indicate the extent of stretching the fabric 807 and the conductive thread 811. In this example, the sensing system 100 can be used to measure interaction with plush toys and interactive clothing. For example, the conductive thread 811 can be woven into the fabric 807 and as the user 118 dances, moves, plays games, etc., environmental surroundings, such as music and lighting, can be controlled by the motion and stretching of the garment, via the interface 170 (FIG. 1).

In another example, the coil of conductive thread 811 can be wrapped around the user's finger or leg or other body part. As the user 118 bends their finger (or leg) the configuration of the coil of conductive thread 811 changes and results in a change in the measured impedance parameter. In this manner, the amount of movement can be measured, thus allowing the development of devices such as, for example, a data glove and motion capture suit, e.g. an instrumented garment that can recognize and record changes in user posture in time, and communicate such information to other systems.

Figure 9A:
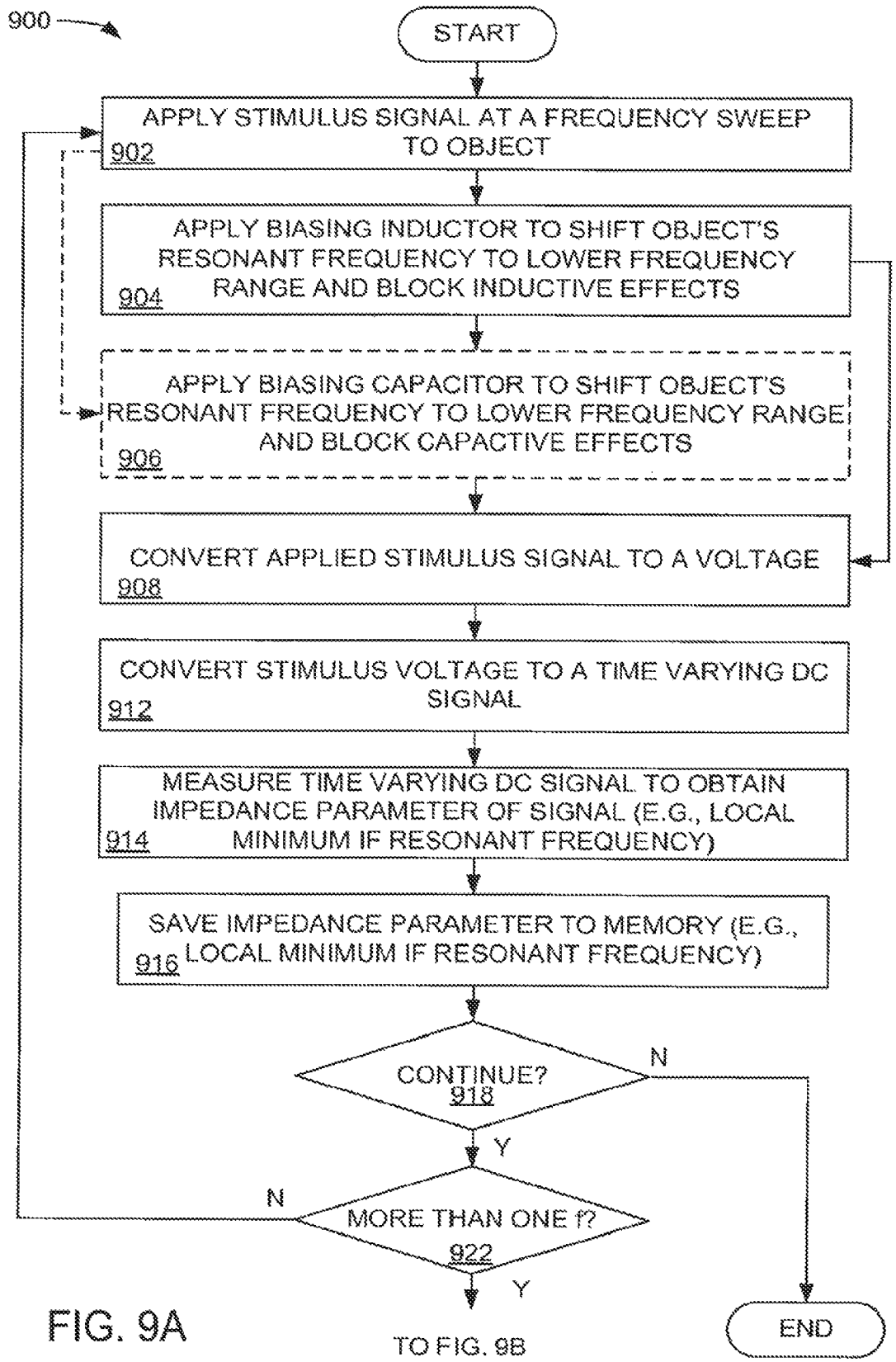
FIGS. 9A and 9B collectively illustrate a flow diagram describing the operation of an embodiment of the method for sensing human activity by monitoring impedance.
Figure 9B:
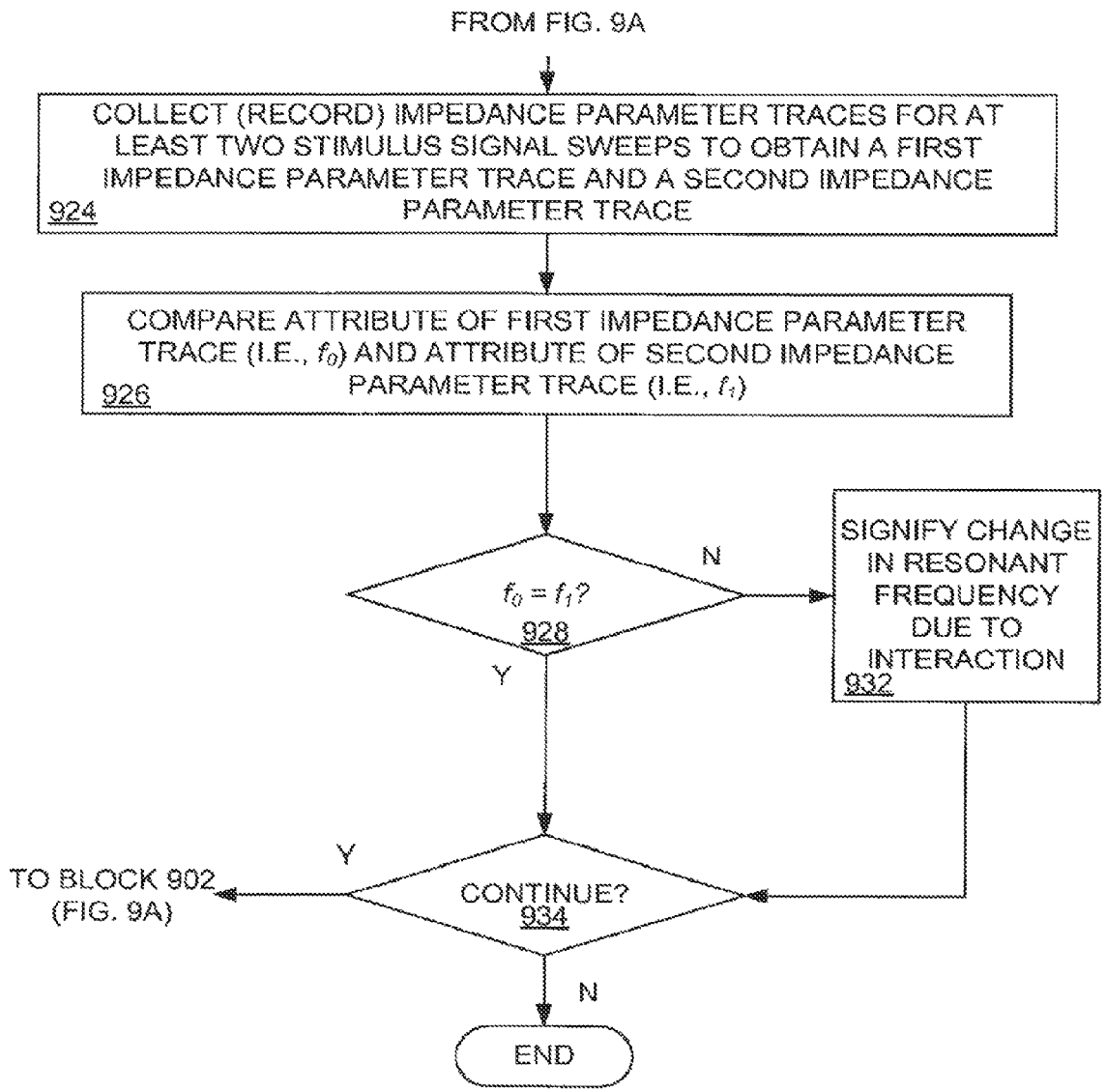

FIGS. 9A and 9B collectively illustrate a flow diagram 900 describing the operation of an embodiment of the method for sensing human activity by monitoring impedance. The blocks in the flow chart of FIGS. 9A and 9B can be performed in or out of the order shown. In addition, at least some of the blocks can be performed in parallel.

In block 902, the signal generator (120, FIG. 1) generates a time varying signal f(t). In an embodiment, the time varying signal f(t) is a 1 KHz to 3.5 MHz, 10V peak-to-peak, sinusoidal frequency sweep. However other ranges of frequencies and signal amplitudes can be used.

In block 904, a biasing inductor shifts the object's resonant frequency to a lower frequency range and blocks inductive effects, thereby facilitating the measurement of small changes in capacitance.

Alternative to block 904, in block 906, a biasing capacitor shifts the object's resonant frequency to a lower frequency range and blocks capacitive effects, thereby facilitating the measurement of small changes in inductance. In block 908, the time varying signal f(t) is converted to a voltage.

In block 912, the time varying voltage signal f(t) is converted to a time varying DC signal. The time varying DC signal defines the alternating voltage at node 138 (FIG. 1).

In block 914, the time varying DC signal is processed to compute one or more impedance parameters of the measured signal. In an embodiment, a local minimum, or other attribute of the signal, is located. In an embodiment, the local minimum of the time varying DC signal corresponds to the resonant frequency, $f_0$, of the object 110. However, other impedance parameters of the signal can also be located that define other electromagnetic resonant attributes.

In block 916, the impedance parameter of the object 110 is saved to the memory 128 (FIG. 1). In an embodiment, the resonant frequency, $f_0$, of the object 110, or another impedance parameter of the signal, is saved to the memory 128 (FIG. 1). For example, the amplitude of the signal trace can be saved to memory 128 (FIG. 1) and used as an indicator of human interaction. The memory 128 can be either or both of local memory and/or memory located on other computing devices and that is accessible using various data transmission technologies, such as wired or wireless connection links. The impedance parameter can also be compared to other impedance parameters that have previously been saved to the memory 128 (FIG. 1) to identify the current impedance parameter.

In block 918, it is determined whether the process is to continue. If the process is to continue, in block 922 it is determined whether there is more than one resonant frequency measurement in memory 128 (FIG. 1). If the process is to continue and there is only one resonant frequency measurement in memory 128 (FIG. 1), the process proceeds to block 902. If the process is to continue and there is more that one resonant frequency, or other parameter of the signal, measurement in memory 128 (FIG. 1), the process proceeds to block 924. In some applications it may be desirable to measure and record a single resonant frequency of an object. In such an application, the process ends after block 918.

In block 924, a first impedance parameter trace and a second impedance parameter trace are collected. In block 926, an attribute of the first impedance parameter trace is compared with a corresponding attribute of the second impedance parameter trace. As an example, the resonant frequency, $f_0$, of the first impedance parameter trace is compared with a resonant frequency, $f_1$, of the second impedance parameter trace. Alternatively, other attributes of the respective impedance parameter traces can be compared.

In block 928, it is determined whether the first resonant frequency, $f_0$, and the second resonant frequency, $f_1$ are substantially equal. If the first resonant frequency, $f_0$, and the second resonant frequency, $f_1$, are substantially unequal, then the process proceeds to block 932, where the change in resonant frequency is noted and signifies human interaction with the object. In alternative embodiments, other impedance parameters of the measured signal can be compared to determine whether there has been human interaction.

If it is determined in block 928 that the first resonant frequency, $f_0$, and the second resonant frequency, are substantially equal, then it is assumed that there is no human interaction with the object 110 and the process proceeds to block 934, where it is determined whether the process is to continue. If the process is to continue, the process returns to block 902 (FIG. 9A).

Swept-Frequency Capacitive Sensing with Living Organisms

Figure 10A:
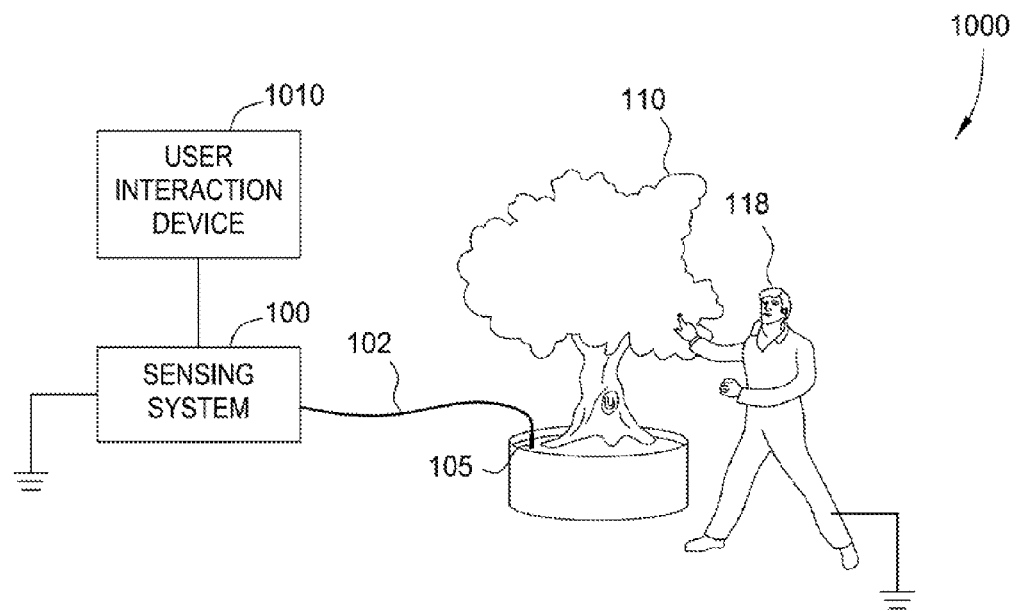
FIGS. 10A-10B are system diagrams for detecting interaction with a living plant, according to embodiments described herein.
Figure 10B:
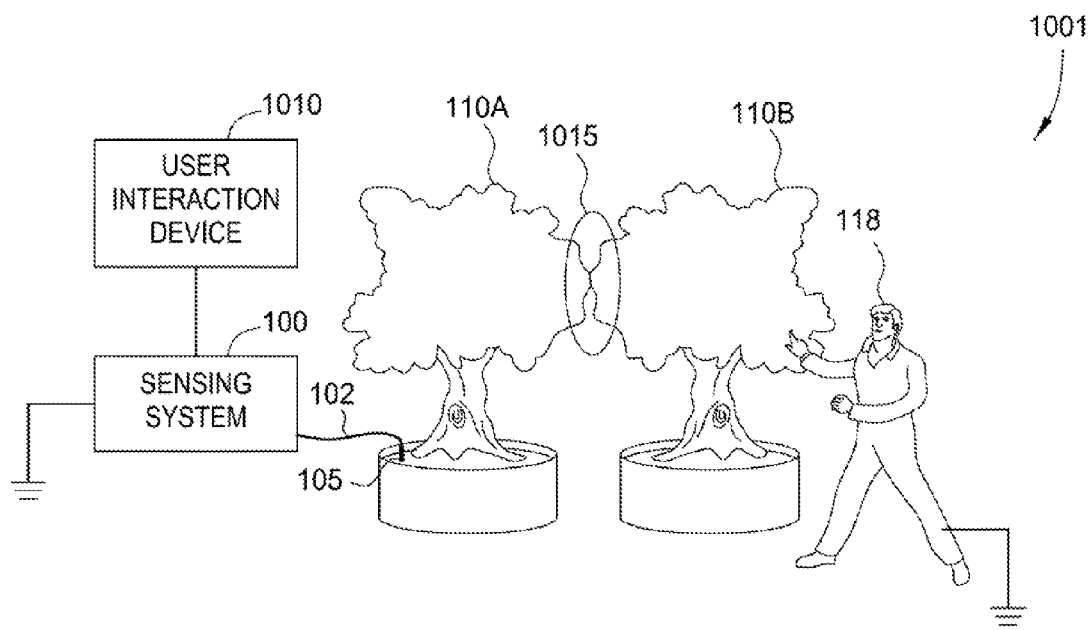

FIGS. 10A-B are system diagrams for detecting interaction with a living plant, according to embodiments described herein. As used herein, a "living" plant is a plant that is organic (i.e., not artificial), and thus, may include plants that are both alive as well as dead. However, in one embodiment, only plants that are alive may be used since these plants may have superior conductive properties relative to plants that are dead. FIG. 10A is a system 1000 that includes a sensing system 100 coupled to a plant 110 via the connection 102 and electrode 105 as discussed in FIG. 1. Moreover, the plant 110 may be electrically coupled to the human or user 118. In one embodiment, the user 118 directly contacts the plant 110 using, for example, an appendage such as a hand or finger. Doing so, changes the capacitance of the electrical path between the sensing system and ground which alters one or more measurable parameters. As discussed above, these measured parameters may include, but are not limited to, resonant frequency, amplitude, impedance, and the like. In one embodiment, the human interaction with the plant 110 changes an impedance curve relative to the static impedance curve with no human interaction.

In one embodiment, the sensing system 100 may sense a change in the static impedance curve even when the user 118 is not directly contacting the plant 110. The sensing system 100 generates a signal that results in the plant 110 emitting an electrical field. As the user 118 moves in this electrical field—i.e., is capacitively coupled to the object—the electrical properties of the user 118 change the impedance curve. Accordingly, the sensing system 100 may be configured to detect the proximity of the user 118 to the plant 110 without the human actually physically contacting the plant 110. Moreover, although the user 118 is shown as being grounded, in other embodiments, user 118 may not need a connection to ground in order to change the impedance curve.

The electrode 105 connecting the plant 110 to the sensing system 100 is shown as being placed in the soil around the plant 110, but in other embodiments may be attached to the plant 110 (e.g., with the use of a clip) or even embedded within the plant 110. The electrode 105 may be located in any location so long as the system 1000 includes a conductive path that carriers the electrical signal generated by the sensing system 100 to the plant 110. In one embodiment, the system 1000 uses the naturally occurring conductive paths in the plant to yield one or more electrical paths coupled to the electrode 105. For example, the electrical signal may flow using the water-carrying veins in the plant 110. As such, the electrical signal may flow in the plant's roots, stems, leaves, trunk, and the like. Although the embodiments discussed herein may used in artificial objects (e.g., artificial plants) that are fabricated to include conductive paths, living plants may have cost advantages relative to artificial plants. That is, living plants may naturally form the conductive paths used to transmit the electrical signal throughout the plant. In addition, living plants may be more durable in, for example, outdoor conditions than artificial plants. Moreover, permitting a user to interact with a living plant via the sensing system 100 and user interaction device 1010 may provide more enjoyment or surprise relative to interacting with a non-living object. As used herein, a human "interacting" with a plant means that the user 118 is electrically coupled to the plant (either directly or indirectly) such that the sensing system 100 can measure the effect of the electrical properties of the user 118 on the generated signal.

After a change in the impedance curve is detected, the sensing system 100 informs the user interaction device 1010 that the user 118 is interacting with the plant 110. In response, the user interaction device 1010 may provide the feedback response to the user 118. The feedback response may be any kind of audio or visual response to the user 118. Non-limiting examples include speech, sound effects, mechanical actions, lighting changes, environmental changes, and the like. As the human interaction with the plant changes—e.g., the user 118 moves closer the plant or firmly grips the plant rather than merely touching the plant—the feedback response produced by the user interaction device 1010 may also change. That is, different human interactions change the impedance curve differently. The sensing system 100 may correlate the different impedance curves to respective actions by the user 118. In one embodiment, the sensing system 100 may be preconfigured to correlate a measured impedance curve to a human action. For example, the sensing system 100 may be connected to a specific plant and configured to identify different human actions to different measured impedance curve. In this manner, the sensing system 100 may be able to identify the difference between the user 118 touching a stem versus touching a leaf of the plant. As the plant changes—e.g., the plant grows or is trimmed—the sensing system 100 may be reconfigured as needed to correlate specific measured impedance curves to particular human interactions.

FIG. 10B illustrates a system 1001 where multiple plants 110A-B may be electrically coupled to the same sensing system 100. Here, plant 110A contacts plant 110B (as shown by circle 1015) such that the electrical signal generated by the sensing system 100 flows through both plants 110A-B. Moreover, the signal may cause both plants 110A and 110B to emit electrical fields. As such, the user 118 may change the measured impedance curve by interacting with either plant 110A or plant 110B. Similar to system 1000, the user 118 may affect the impedance curve by directly touching the plants 110A-B or by affecting the electrical field emitted by the plants 110A-B. Although only two plants 110 are shown connected in series, any number of objects may be connected in this manner.

Alternatively, the sensing system 100 may include a plurality of electrodes 105 that are connected to different plants 110 that may be electrical insulated relative to each other. Here, the system 1001 may detect human interaction with any of the plants coupled to the electrodes 105. As such, the system 1001 may include a plurality of electrodes 105 and plants coupled in parallel such that a user 118 interacting with any one of the plants changes the impedance curve and results in the user interaction device 1010 providing a feedback response.

Figure 11A:
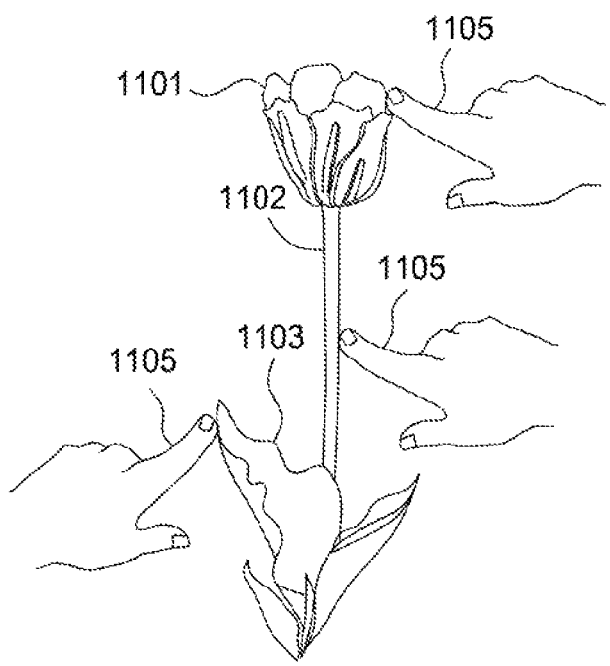
FIGS. 11A-11F illustrate different techniques for physically interacting with a living plant, according to embodiments described herein.

FIGS. 11A-F illustrate different techniques for physically interacting with a living plant, according to embodiments described herein. FIG. 11A illustrate a plant with a flower 1101, stem 1102 and leaf 1103. The finger 1105 may interact with the plant by touching the specific anatomic portion of the plant. Moreover, in one embodiment, the sensing system is able to detect which anatomic portion of the plant the finger 1105 is touching. That is, the finger 1105 may change the impedance curve differently when the finger 1105 touches each of the different portions of the plant. Based on the measured impedance curve, the sensing system may send different data to the user interaction device (not shown). For example, if the finger 1105 touches the stem 1102, the user interaction device may provide a different feedback response than when the finger 1105 touches the leaf 1103.

Figure 11B:
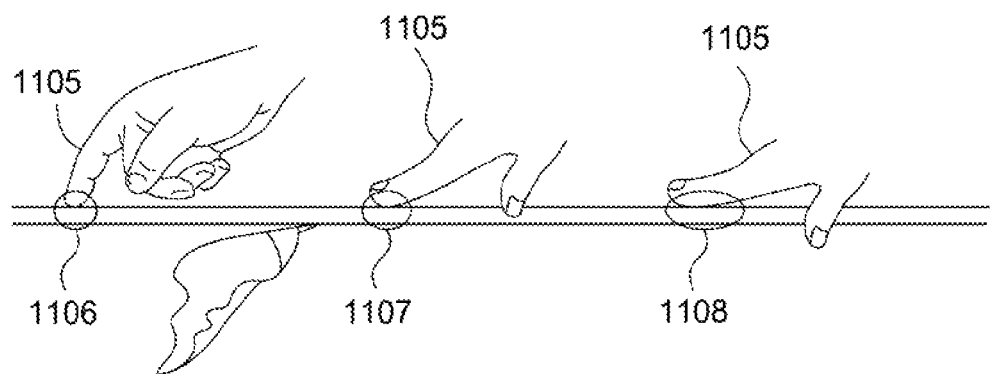

FIG. 11B illustrate the finger 1105 touching the plant with varying contact surfaces. As shown by circle 1106, the finger 1105 touches the plant lightly such that only a small portion of the tip of the finger 1105 touches the plant. As shown by circle 1107, the finger 1105 is either pressed harder against the plant or orientated such that more surface area of the finger 1105 touches the plant. As shown by contact area 1108, the finger 1105 is laid on top of the plant. Each of the three embodiments may cause the electrical properties of the human to affect the electrical signal in the plant differently. For example, contacting the plant as shown by circle 1106 may shift the resonant frequency less than when contacting the plant as shown by circle 1107. The sensing system may be preconfigured to correlate the measured impedance curve to one of the shown user interactions and pass this information to the user interaction device.

Figure 11C:
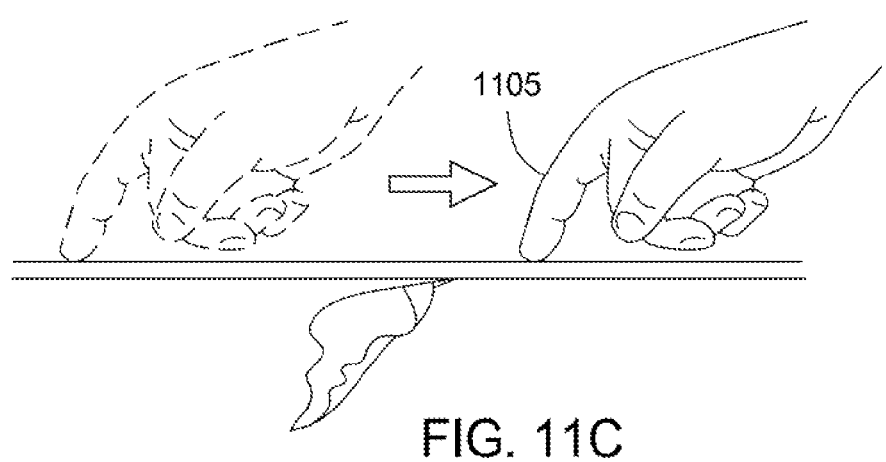

FIG. 11C illustrates the finger 1105 sliding along the plant. That is, the finger 1105 moving across the stem may change the impedance curve in some predictable manner which can be detected by the sensing system. Moreover, the manner in which the sliding action changes the impedance curve may change based on how hard the finger 1105 is pressed on the surface or how fast the finger 1105 slides along the surface. Accordingly, the sensing system may be configured to detect the different sliding actions which may prompt the user interaction device to provide custom feedback based on each sliding action.

In one embodiment, the sensing system may require the measured impedance curve to remain the same for some predefined period of time before indicating to the user interaction device how the user is interacting with the plant. For example, the sensing system may require the user to slide the finger 1105 at a substantially constant rate for at least a second before determining if the measured impedance curve correlates to a human interaction with the plant—i.e., the sensing system ensures that the measured impedance curve is substantially constant over multiple samples. If the user stopped sliding the finger 1105, or slid the finger at a substantially slower or faster rate and substantially changed the measured impedance curve, the sensing system may not identify a particular user interaction. Of course, the sensing system may also measure the impedance curve for a predefined amount of time for the other actions shown in FIGS. 11A-F—e.g., requiring the user to touch the flower for at least two seconds before indicating to the user interaction device that the user is touching the flower.

In one embodiment, the structure or the physiology of the plant defines the type of actions the user can use to interact with the plants. For example, in long stem plants (e.g., bamboo or palm trees), the sensing system may be configured to recognize touching and sliding fingers along the stem while touching the leaves may not be detected. For large-leaf plants, the sensing system may be configured to identify the user touching leaves, stem, trunk, or roots as different interactions. Moreover, the sensing system may distinguish the actions based on the motion (sliding or stationary) as well as pressure. For long leaf plants, interacting with the plant may be limited to sliding the finger along the leaves. Furthermore, the user may interact with water based plants floating in water. Here, the user may interact with the plant by touching the water, by touching the plant directly, or by affecting the electrical field surrounding the plant.

Figure 11D:
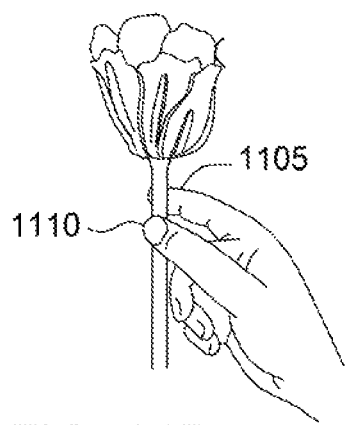
Figure 11E:
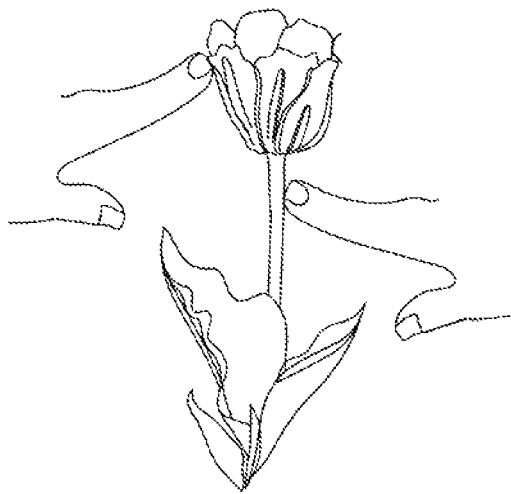
Figure 11F:
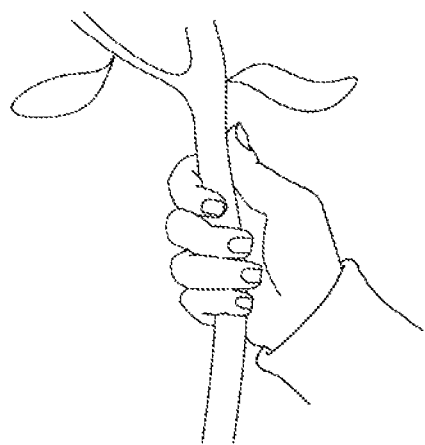

FIG. 11D illustrates the user touching the plant with two fingers. As shown, the user may use the first digit 1105 and a second digit 1110 on the same hand to touch the same portion of the plant—e.g., the stem. This action may change the impedance curve relative to touching the stem with only one finger. FIG. 11E illustrates two fingers, which may or may not be on the same hand, touching different anatomic portions of the plant. FIG. 11F illustrates a user grasping the plant using the palm of the hand. Similarly, the user may use just the palm of the hand of other body surface pressed against the plant. These examples provided above may also result in a unique change to the impedance curve that can be detected by the sensing system.

Moreover, the different actions shown in FIGS. 11A-F may be combined to generate additional actions. For example, sliding the finger at a particular rate may change the impedance curve and result in different feedback than sliding the finger at the same rate but with a different pressure between the finger 1105 and the plant. Or grasping the plant while touching the plant's stem may illicit a different feedback response than grasping the plant and touching a leaf. Furthermore, the examples shown in FIG. 11A-F are illustrative only and the present disclosure is not limited to such. One of ordinary skill in the art will recognize a variety of different ways to detect and identify different actions (or combination of actions) between a user and a plant.

Although FIGS. 11A-F illustrate using fingers, the invention is not limited to such but may include the user touching the plant with an elbow, foot, shoulder, etc. or using conductive elements—e.g., metallic objects—to interact with the plant by changing the frequency-swept impedance curve relative to the static impedance curve.

Figure 12A:
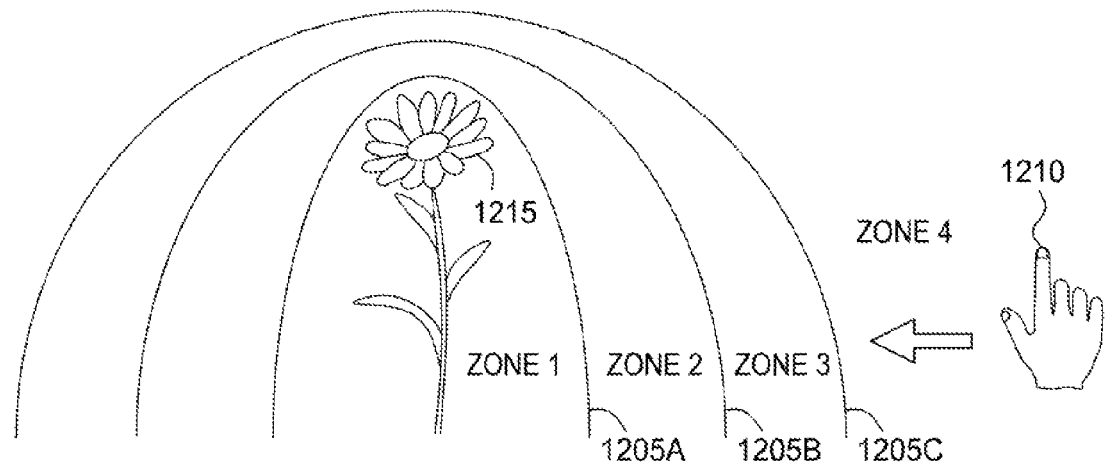
FIGS. 12A-12C illustrate changing the level of interaction based on measuring the proximity to a interactive, living plant, according to embodiments described herein.
Figure 12B:
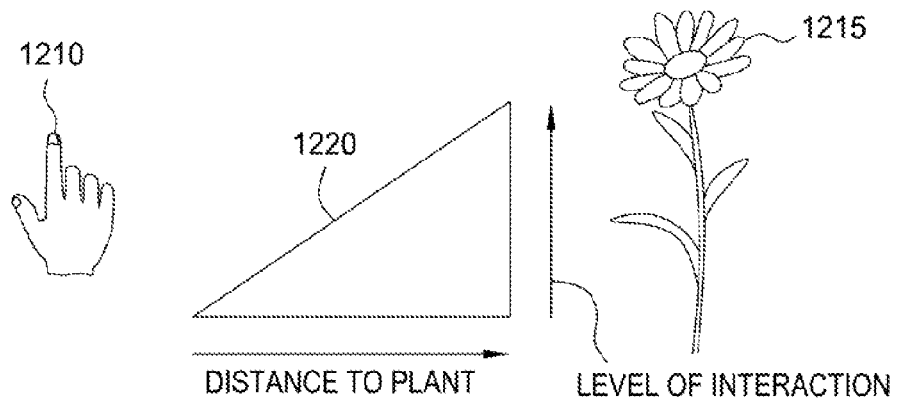
Figure 12C:
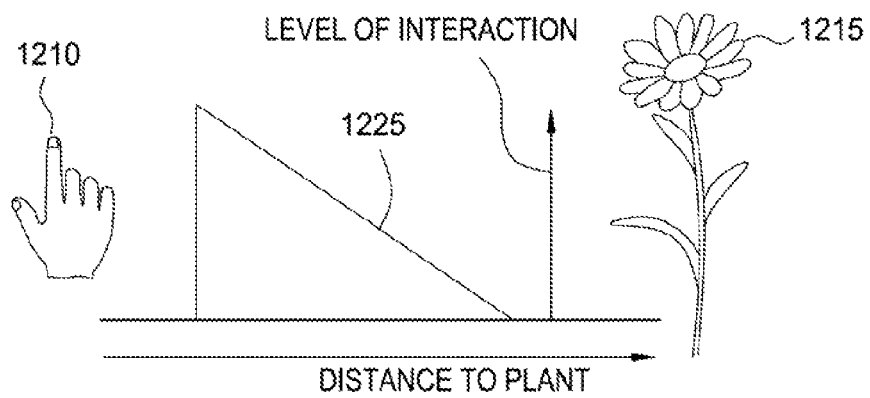

FIGS. 12A-12C illustrate changing the level of interaction based on measuring the proximity of a user to an interactive plant, according to embodiments described herein. Specifically, FIG. 12A illustrates establishing one or more triggers 1205A-C that change the feedback provided to the user. In the embodiment shown, the triggers 1205A-C are boundaries between different zones (Zones 1-4) that divide the volume or space surrounding the plant 1215. Zone 1 is the space closest to the plant 1215, Zone 2 is the space surrounding Zone 1, and so forth. The sensing system may be preconfigured such that as the hand crosses each trigger 1205A-C, a different feedback response is triggered. As explained earlier, if the plant 1215 is coupled to the sensing system (not shown), the electrical signal may emit an electrical field surrounding the plant 1215. Typically, the strength of the electrical field attenuates as the distance from the source of the electrical field (i.e., the electrical signal in the plant 1215) increases. Nonetheless, the sensing system coupled to the plant 1215 may be able to detect when the hand 1210 moves into this electrical field since the electrical properties of the hand 1210 changes the measured impedance curve. Moreover, as the hand 1210 moves closer to the plant 1215, where the electrical field is stronger, the hand 1210 may have a greater effect on the impedance curve. Accordingly, the sensing system may be able to deduce the proximity of the hand 1210 to the plant 1215—i.e., which zone the hand 1210 is located—based on the measured impedance curve.

In one embodiment, the triggers 1205A-C may be different discrete impedance curves such that as the hand 1210 changes the measured impedance curve to match one of the triggers 1205, the user interaction device may provide a custom feedback response to the user. Stated differently, the triggers 1205A-C may be discrete switches that permit the user interaction device to provide different feedback response based on proximity. For example, the plant 1215 may be located in a room full of other plants. In order to find the interactive plant, the user may move towards each plant. If the user moves into zone 4, the user interaction device may illuminate a first light. As the user moves into closer zones, the user interaction device may continue to illuminate additional lights. However, if the user guesses incorrectly and crosses a trigger 1205 into a zone further from the interactive plant 1215, the user interaction device may turn off one of the lights. When the user actually contacts the plant 1215, the user interaction device may produce a congratulatory statement. In this manner, the ability of the sensing system to determine the proximity of the user to the plant may be combined with the ability to identify unique physical interactions between the user and the plant—e.g., touching the plant as shown in FIGS. 11A-F.

FIGS. 12B and 12C illustrate two different embodiments that may alter the feedback continuously based on proximity. In contrast to the discrete triggers shown in FIG. 12A, in FIGS. 12B and 12C the feedback may alter as updated impedance curves are measured by the sensing system. As shown, the area around the plant 1215 is not broken up into zones. Instead, the sensing system sends an update to the user interaction device based on a predefined time period during which one or more impedance curves are measured or sampled—e.g., every second. If the curve has changed, the level of interaction may also change. In one embodiment, the level of interaction includes the strength of the feedback response (e.g., the decibel value of an output sound or the luminance of a light). The graph 1220 indicates that as the distance between the hand 1210 and the interactive plant 1215 decreases, the level of interaction increases. For example, the user could be blindfolded and tasked with bringing water to the interactive plant 1215. As the user moves closer to the plant 1215, a sound may play louder. But as the user moves away from the plant 1215, the sound may become quieter.

Graph 1225 in FIG. 12C illustrates an embodiment where the level of interaction decreases as the distance between the hand 1210 and the plant 1215 decreases. Thus, the greatest level of interaction may occur when the user is at the greatest detectable distance from the plant 1215. Such a relationship between the distance and the level of interaction may be desired where the user is encouraged to interact with the plant without touching the plant. For example, the plant 1215 may be delicate or not able to withstand constant physical contact. As the user moves closer to the plant 1215, the interaction may decrease until it ceases completely. The interaction may resume as the user moves away from the plant 1215. Note that graphs 1220 and 1225 are for illustrative purpose only. In other embodiments, the level of interaction may increase as the distance between the hand 1210 and plant 1215 decreases but, after a set distance, the level of interaction may decrease as the distance continues to decrease.

In one embodiment, the sensing system may consider the speed or rate at which the distance between the hand 1210 and the plant 1215 changes. For example, if the distance between the objects decreases above a predefined rate, instead of only decreasing the level of interaction at a faster rate, the interactive device may issue a warning such as "Don't get to close to me or I'll stop talking." This additional functionality may be used in any of the embodiments shown in FIGS. 12A-C. For example, if the hand 1210 crosses two triggers 1205 within a predefined period of time (e.g., less than two seconds) the interactive device may provide an additional feedback response. Alternatively, instead of providing an additional response, the interactive device may use a different response if the user is approaching too fast or too slow.

Figure 13A:
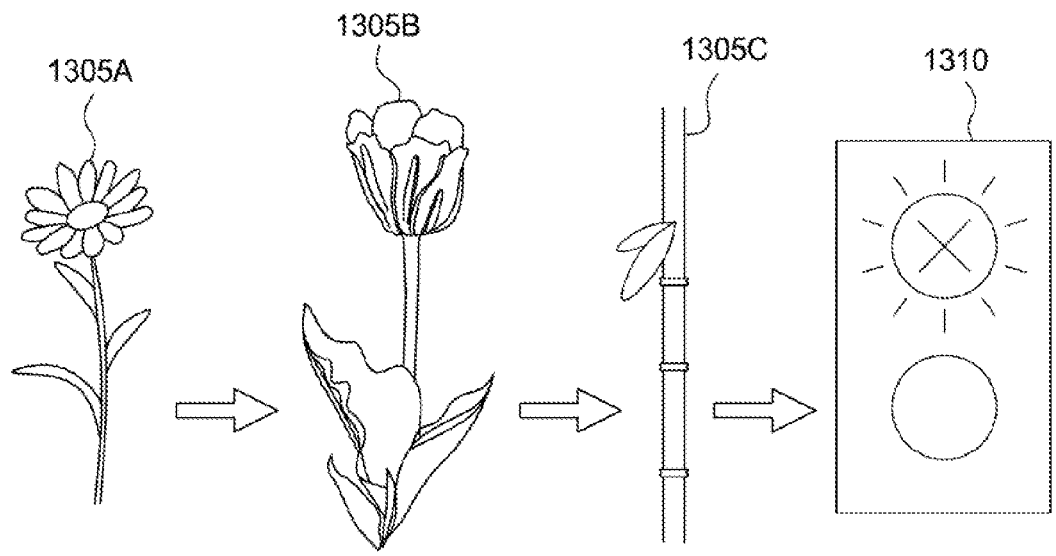
FIGS. 13A and 13B illustrate providing interactive feedback based on sequential interaction with living plants, according to embodiments described herein.
Figure 13B:
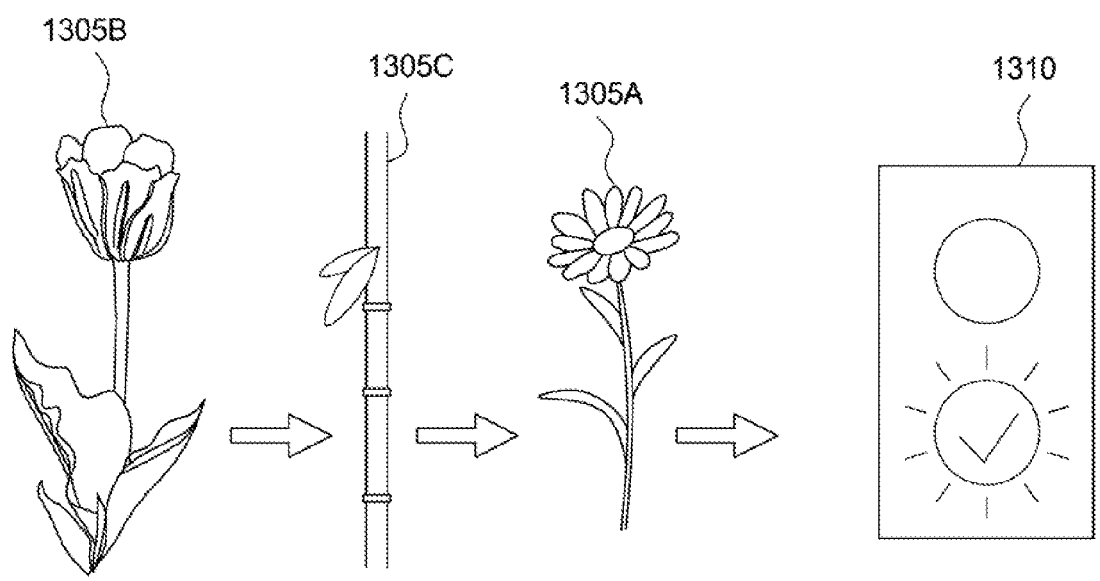

FIGS. 13A-13B illustrate providing interactive feedback based on sequential interaction with living plants, according to embodiments described herein. In FIG. 13A, the different plants 1305A-C may be connected to individual sensing systems. Moreover, the individual sensing systems may all be connected to a shared interactive device 1310. The individual sensing systems may each determine if a user has, for example, touched the plant 1305 coupled to the system. As shown in FIG. 13A, the user first touches plant 1205A, then plant 1305B, and finally plant 1305C. In one embodiment, the interactive device 1310 may include logic or a mechanical or electrical switch (e.g., a relay) that uses as an input respective signals from the individual sensing systems that indicate whether a user has interacted with a plant 1305. Based on the input, the interactive device 1310 determines if the user interacted with the plants 1305 in a predefined order. Because in FIG. 13A the user did not interact with the plants 1305A-C in the correct order, the interactive device 1310 provides negative feedback to the user. However, FIG. 13B indicates that when the user does interact with the plants 1305A-C in the correct order (i.e., plant 1305B, then plant 1305C, and finally plant 1305A), the interactive device provides positive feedback.

In another embodiment, the order by which a user interacts with multiple plants (i.e., multiple plants connected to individual sensing systems) could be used to provide continual feedback. For example, the interactive device 1310 may provide a feedback reaction at each step. If the user interacts with plant 1305B first, the interactive device may play music. If the user then interacts with plant 1305A, the interactive device may output a noise indicating the choice was incorrect. If the user corrects the mistake by interacting with plant 1305C, the interactive device 1310 may, for example, play music that supplements to the music played when plant 1305B was touched. In other embodiment, the order may follow along with a guide or a story provided by the user. The user may have a guide such as a pamphlet, book, or electronic device with instructions for interacting with the plants. If the user follows the instructions, the interactive device 1310 provides feedback that may supplement information in the guide. For example, the guide may be a story about the plants 1305 where each time one of the plants 1305 is mentioned in the story (i.e., in a predefined order) the user can touch the respective plant 1305 and receive a feedback response from the interactive device 1310.

FIGS. 14A-14B illustrate providing interactive feedback based on multiple individuals interacting with the same living plant, according to embodiments described herein. In FIG. 14A, multiple individuals 1410A-B may interact with the same plant 1405 simultaneously. In this embodiment, the sensing system coupled to the plant 1405 may be preconfigured to determine the difference between one individual 1410 interacting with the plant 1405 and two individuals 1410A-B interacting with the plant. Although not shown, the sensing system may also be configured to distinguish between two individuals 1410 interacting with the plant 1405 and three individuals interacting with the plant 1405, and so forth. In one embodiment, the sensing system is configured to detect a predictable change in the impedance curve each time a new individual 1410 begins to interact with the plant 1405. For example, each individual 1410 may have similar electrical properties (e.g., the capacitance of the individual body is substantially the same) thereby causing a predictable change in the impedance curve—e.g., the same shift in the resonant frequency or change in amplitude of a peak. The sensing system may detect these discrete changes and identify a number of individuals 1410 interacting with the plant 1405. The sensing system may determine the number of individuals 1410 interacting with the plant 1405 and transmit this information to the user interactive device which may provide different feedback based on the number.

In another embodiment, the sensing system may be configured to determine whether multiple people are touching each other. For example, two or more individuals 1410 may grasp hands while only one of the individuals interacts with the plant 1405. As more individuals are added to the group—i.e., more individuals grasp hands—the sensing system may be able to determine, based on the changing electrical properties, how many individuals are in the group. For example, when a first individual interacts with the plant 1405, the interactive device may issue an instruction for four more people to interact directly with the plant 1405 (e.g., touch a leaf or stem) or that multiple individuals grasp hands while the first individual continues to interact with the plant 1405. As more people touch the plant 1405 or grasp hands, the sensing system may detect the change which results in the interactive device providing additional feedback—e.g., "I see that you've added another person to your group, only two more to go!" Once the instruction is has been carried out, the interactive device may provide a predefined feedback response.

FIG. 14B illustrates multiple people interacting with an interactive plant 1405 sequentially rather than simultaneously. In the first step, the user 1410A interacts with the plant 1405. For example, the sensing system coupled to the plant 1405 may determine that the user 1410A is proximate to the plant as discussed in FIGS. 12A-C. In one embodiment, once the user 1410A touches the plant, the interactive device outputs the feedback response 1415A. Before providing feedback response 1415B, however, the user interaction device may first wait to determine if user 1410A is no longer proximate to the plant. For example, the sensing system may use the triggers shown in FIG. 12A where the user 1410A is determined to be no longer proximate to the plant 1405 once she crosses the last trigger 1205C. Specifically, if the user 1405A crosses the trigger 1205B and subsequently crosses trigger 1205C, the sensing system determines the user 1410A is no longer proximate to the plant 1405 and informs the user interaction device.

In the next step, the sensing system may detect that user 1410B is now proximate to the plant by, for example, the user 1410B changing the electrical field emitted by the plant. In one embodiment, the sensing system is configured to distinguish between user 1410A and user 1410B. For example, adult humans may have substantially different electrical properties than children. In order for the interactive device to provide the feedback 1415A-C, the sensing system may require that the plant 1405 interact with a child user, then an adult user, then a child user, etc. Thus, if the user 1405A (a child) attempts to leave the proximity of the plant 1405 and then return, the sensing system determines that a child is still interacting with the plant and does not instruct the interactive device to provide the feedback 1415B. Or the interactive device may provide negative feedback that instructs how to correct the mistake—e.g., "If you want to hear the rest of my story, an adult must come near." Assuming that user 1410B is an adult, once she interacts with the plant 1405 the next feedback response 1415B is outputted.

In the next step, user 1410B leaves the proximity of the plant 1405 and the next user 1410C may interact with the plant 1405. Again, the sensing system may require that user 1410B leave the detectable proximity of the plant 1405 before providing the feedback response 1415C. Like in the previous step, the sensing system may also require the next user 1410C have different electrical properties than the previous user 1410B before permitting the feedback response 1415C—e.g., one user is an adult while the other is a child. Moreover, although the electrical properties between human adults may be similar, they are not exactly the same. Accordingly, the sensing system may indentify how each user 1410 changes the impedance curve based on their unique electrical properties—e.g., the users' electrical properties may be different because of physical or chemical differences or because of the clothing they wear—and uniquely identify each user 1410 interacting with the plant 1405. In this manner, the sensing system may ensure that multiple sequential people interact with the plant 1405 rather than one person leaving the proximity of the plant and returning. Of course, the sensing system may be configured such that each time a user 1405 is no longer proximate to the plant, the next user 1405 that approaches the plant is assumed to be different from the previous user.

FIGS. 15A-15D illustrate using an interaction with a living plant to trigger a mechanical or environmental action, according to embodiments described herein. In the system 1500, the plant 1505 may be placed in a mechanical actuator 1515 that may also serve as a pot for the plant 1505. Although not shown, the mechanical actuator 1515 may also house the sensing system which determines when the user 1510 interacts with the plant 1505. Further still, the mechanical actuator 1515 may be a type of user interactive device that is triggered based on the sensing system detecting user interaction. For example, in FIG. 15B the user 1510 interacts with the plant 1505 which causes the mechanical actuator 1515 to shake the plant 1505 to make a rustling sound. In addition, the system 1500 may include a user interaction device that could make a sound such as an animal noise to provide the user 1510 with the impression that an animal is causing the plant 1505 to shake. Moreover, because the sensing system may trigger the mechanical actuator 1515 based on the user 1510 being proximate to the plant 1505 or only brushing up against the plant rather than touching the plant for the intent of causing feedback response, the system 1500 may surprise the user 1510 and enhance her interaction with the plant 1505.

In other embodiments, the mechanical actuator 1515 may be further integrated with the interactive plant 1505. For example, the mechanical actuator may be a robotic frame which the interactive plant 1505 (e.g., a vine or shrub) covers. Once the user interacts with the plant 1505, the robotic frame may move, thereby moving the plant 1505. In this manner, the user 1510 could interact with the plant by, e.g., shaking the plant's "hand" or watching the plant 1505 wave.

Figure 15A:
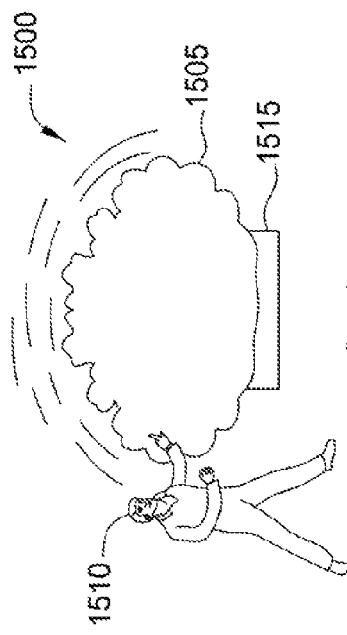
FIGS. 15A-15D illustrate using an interaction with a living plant to trigger a mechanical or environmental action, according to embodiments described herein.
Figure 15C:
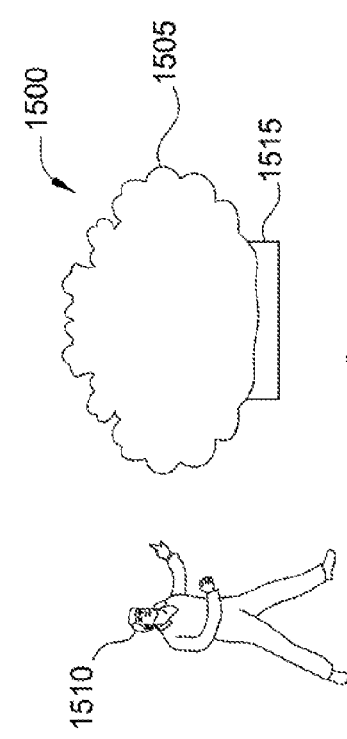
Figure 15B:
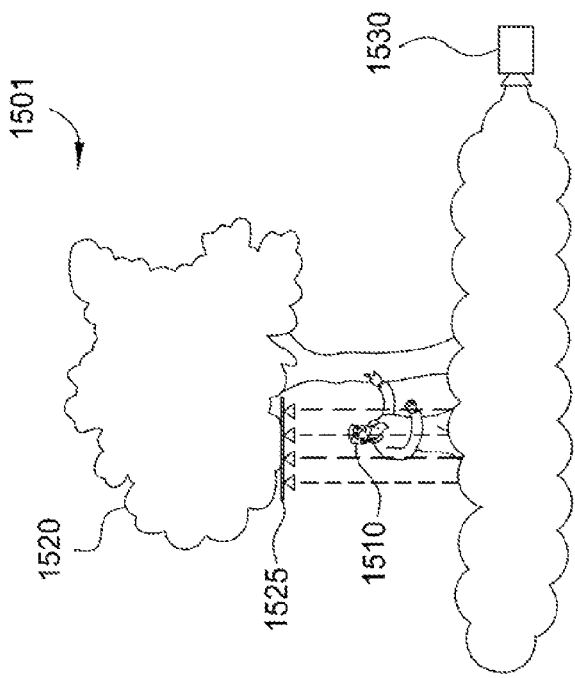

In FIG. 15C, the system 1501 includes a user interaction device 1525 mounted in the plant 1520 as well as another user interaction device 1530 located away from the plant 1520—e.g., external to the plant 1520. Nonetheless, the sensing system coupled to the interactive plant 1520 may be used to trigger both interactive devices 1525 and 1530.

Figure 15D:
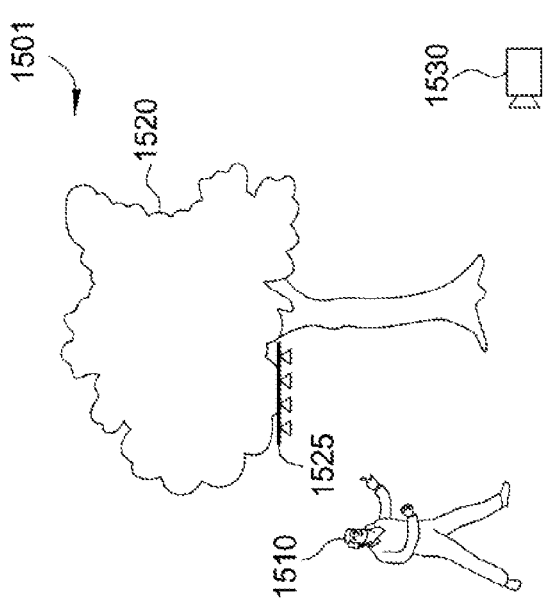

As shown in FIG. 15D, the sensing system detects that the user 1510 interacts with the plant 1520. In response, the user interaction device 1525 provides a feedback response. Here, the device 1525 is a sprinkler system that drips water on the user 1510. This action could simulate, for example, rain (an environmental condition) or that the plant 1510 is crying. Additionally, the same user action may also trigger a second feedback response by the user feedback device 1530—i.e., a fog machine. In this manner, the feedback response may be any number of different response that may or may not be directly correlated to the plant but are triggered by the human interaction with the plant. For example, other environmental responses include blowing air, dispensing of a scent, lighting changes, temperature changes, mist, smoke, simulated earthquake, and the like. Furthermore, the feedback response may be any number of audio response (e.g., voice, stories, music, sound effects, etc.) or visual responses (e.g., projecting light onto the plants, people, the surrounds, etc.). In one embodiment, the type of feedback response may depend on the time of day. For example, in an outside area, during the day the response may be mist, but when it is dark, the feedback response may be a change in the lighting.

In another embodiment, the interactive, living plants may be placed or incorporated with artificial plants or the user interactive device. For example, the pot that holds the interactive plant may be designed to look like part of the living plant. However, the pot may be a user interactive device that includes displays, speakers, lasers, mechanical actuators, etc. that associates the feedback response with the living plant. Similarly, the artificial plants may be user interactive devices equipped with LEDs, lasers, UV light, or other display technologies that are triggered by sensing a user's presence using the living plant.

Figure 16:
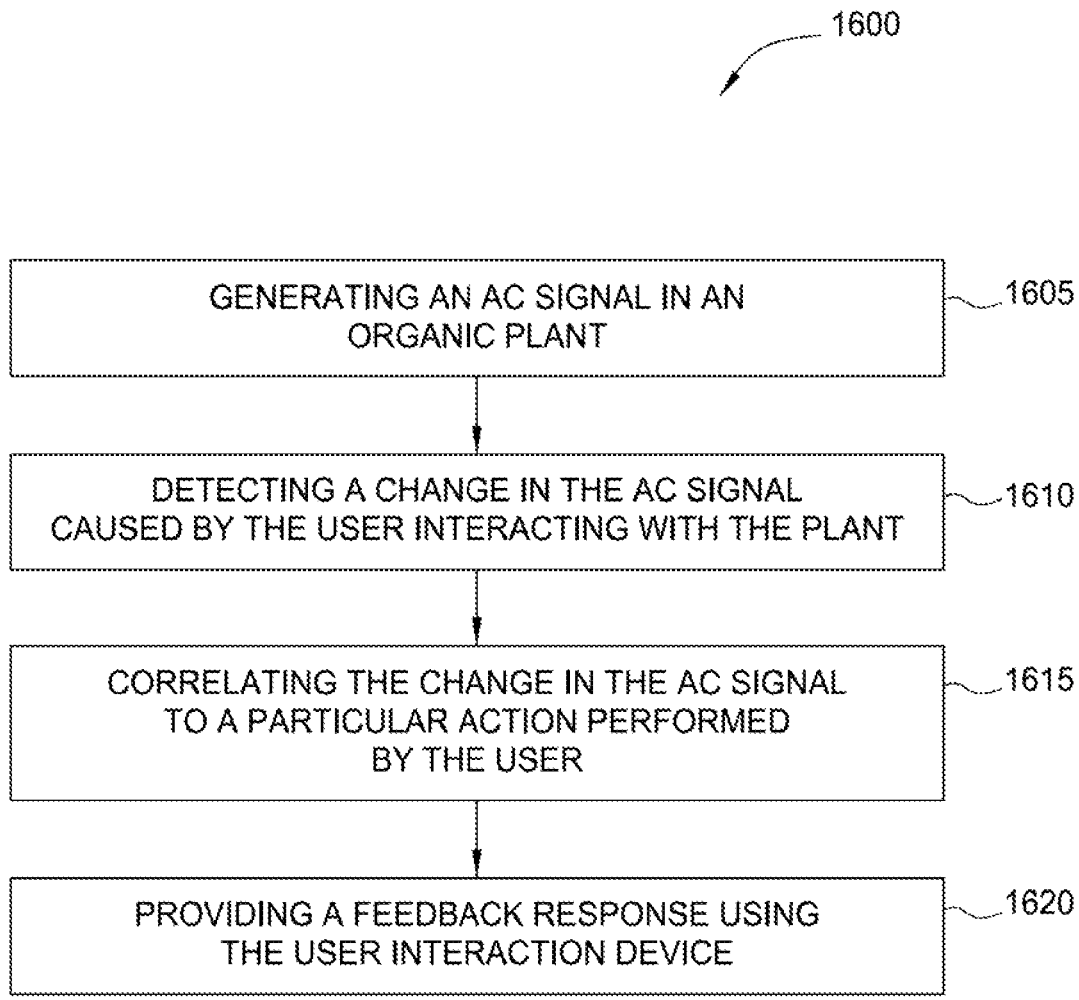
FIG. 16 is a method of providing a feedback response based on user interaction with a living plant, according to one embodiment described herein.

FIG. 16 is a method 1600 of providing a feedback response based on user interaction with a living plant, according to one embodiment described herein. At block 1605, a sensing system generates an AC signal that is transmitted through one or more portions (or throughout) the living plant. In one embodiment, the AC signal travels through the natural conductive paths in the plant such as water-carrying veins.

At block 1610, the sensing system may detect a change in the AC signal caused by the user interacting with the plant. In one embodiment, the user becomes electrically coupled to the plant by directly contacting the plant such that the AC signal is transmitted from the plant to the user. Furthermore, the user may be coupled to a common reference point (e.g., earth ground) as the sensing system. Alternatively, the user may be indirectly coupled (e.g., capacitively coupled) to the reference point. For example, the user becomes electrically coupled to the plant by affecting the electrical field emitted by the plant from the AC signal but does not directly contact the plant. The user is capacitively coupled to the plant such that the AC signal flows through the user but the user does not physical contact the plant. Regardless whether the user is directly or indirectly coupled to the plant, the electrical properties of the user, e.g., the reactance value associated with the user, changes a parameter of the AC signal. As described in FIGS. 1 and 2A-2B, the sensing system detects the change and may determine the user is interacting with the plant.

At block 1615, either the sensing system or the user interaction device correlates the change in the AC signal to a particular action performed by the user. As shown in FIGS. 11A-F and 12A-C, the action may be, for example, a specific pressure applied to the plant, what specific anatomic part of the plant the user is touching, the motion of the touch, the number of contact points, the size of the contact area, the distance traversed by the user proximate to the plant, or the number of users interacting with the plant. The sensing system may be configured to correlate the change in the measured impedance curve to a human action or a combination of actions. For example, the change may be the peak of the resonant frequency of the impedance curve shifting by 40 Hz while the amplitude of the peak falls by 300 mV. The sensing system may be configured such these changes in the curve are correlated to the user touching the leaf of the plant while sliding the finger. The sensing system may be configured to include any number of other correlations that identify additional human interactions with a plant.

At block 1620, the user interaction device provides the feedback response based on the identified action. For example, the user interaction device may provide a different response for each action or group of actions. Additionally, the interaction device may provide a response only if a certain action is detected. For example, the user interaction device may output music if the user touches the plant's leaf, output both music and simulated fog if the user touches a stem, but do nothing if the user touches the trunk. In this manner, the feedback response may be determined based on the user interaction with the plant.

Figure 17:
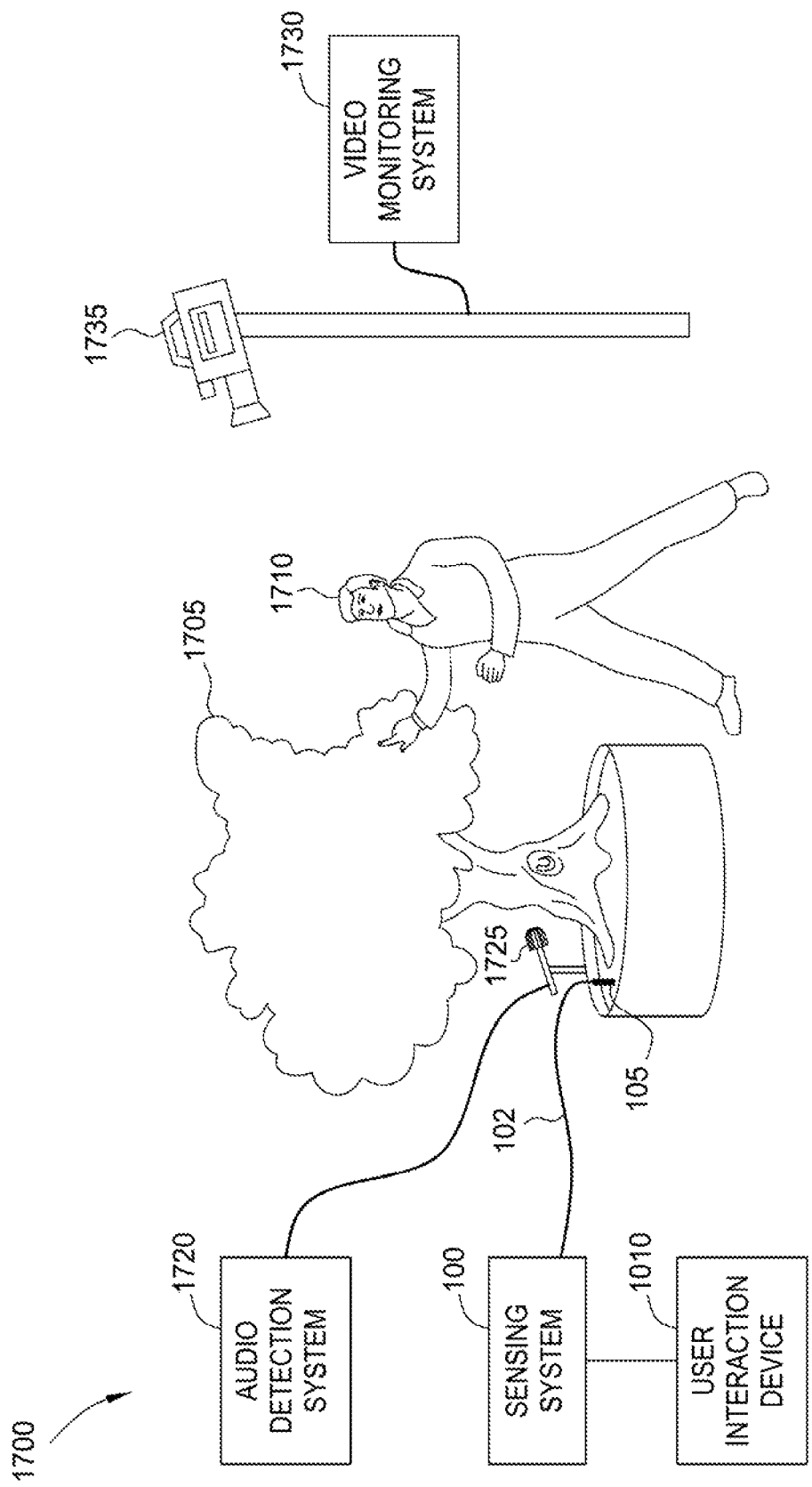
FIG. 17 is a system for combining different monitoring and detection techniques for determining interaction with a living plant, according to embodiments described herein.

FIG. 17 is a system 1700 for combining different monitoring and detection techniques for determining interaction with a living plant, according to embodiments described herein. The system 1700 is similar to the system 1000 of FIG. 10A in that system 1700 includes sensing system 100, user interaction device 1010, connector 102, and electrode 105. System 1700 also includes plant 1705 and user 1710 which may interact using, for example, any of the embodiments discussed above. In contrast to system 1000, the sensing system 100 or user interaction device 1010 in system 1700 may further rely on information gathered by a secondary detection system such as audio detection system 1720 or video monitoring system 1730. In generally, the secondary detection system may transmit data to the user interaction device 1010 that aids in identifying the feedback response or responses to provide to the user 1710.

The audio detection system 1720 includes one or more microphones 1725 or audio sensors for detecting sounds in the system 1700. In one embodiment, the audio detection system 1720 may recognize voices or speech patterns of the user 1710. For example, the user 1710 may be able to have a simulated conversation with the plant 1705 using the audio detection system 1720. The sensing system 1010 may detect the presence of the user 1710 using the sensing system 100 and ask the user 1710 a question. The user's response is detected by the audio detection system 1720 which may transmit the response (or appropriate data representing the user's response) to the user interaction device 1010 for further interaction with the user 1710—e.g., the user interaction device 1010 asks another question based on the user's response or causes some mechanical or visual response. In another example, the audio detection system 1720 may compare the user's voiceprint with a plurality of known voiceprints. For example, before entering a theme park, the user 1710 may state his name which is used to identify the user 1710. Once the plant 1705 detects the user 1710 and the user interaction device 1010 asks a question, the user's response may be compared to the stored voiceprint to determine the user's identity. The user interaction device 1010 may customize the feedback response based on the both the user's interaction with the plant 1705 and the user's identify. To enable the sensing system 100 and audio detection system 1720 to work together, the audio detection system 1720 may be coupled to the user interaction device 1010 (or the sensing system 100) using any wired or wireless communication technique.

The video monitoring system 1730 includes a camera 1735 which may monitor the area around the plant 1705. The video monitoring system 1730 receives the raw data from the camera 1735 and may process the data to, e.g., track users around the plant 1705, perform facial recognition, count the number of users in the area, interpret physical motions, and the like. For example, the video monitoring system 1730 may be used in the embodiment shown in FIG. 14B where different users interact sequentially with the plant 1405. That is, the sensing system 100 may determine when a user interacts with the plant 1705 while the video monitoring system 1730 ensures that the subsequent user 1710 is indeed different from previous users by using, for example, facial recognition. In another example, after a user 1710 interacts with the plant 1705, the user interaction device 1010 may instruct the user 1710 to perform a certain motion. Using the video monitoring system 1730, the system 1700 may determine whether the user 1710 performed the motion. The information captured by the video monitoring system 1730 may be transmitted, either wired or wirelessly, to the user interaction device 1010 to affect the feedback responses provided to the user 1710.

The system 1700 may use other secondary detection systems besides the ones shown in FIG. 17. For example, the user interaction device 1010 may request the user 1710 hang or attach certain objects on the plant's 1705 branches. The objects may be embedded with a radio frequency identification (RFID) tag. A RFID transceiver may be located in the system 1700 that determines when a RFID tag is hung on the plant 1705. Once the task is complete, the RFID transceiver may inform the user interaction device 1010 which provides the appropriate feedback response. In another embodiment, the system 1700 may include a moisture monitor in the soil around the plant 1705. If the moisture monitor determines that the soil is dry, the monitor may inform the user interaction device 1010. Once the sensing system 100 determines that the user 1710 is close to the plant 1705, the user interaction device 1010 may ask the user 1710 to water the plant 1705. As the moisture monitor determines the water level in the soil is increasing, it may send a signal to the user interaction device 1010 which thanks the user 1710. However, the provided examples are illustrative only. One of ordinary skill in the art will recognize the other secondary detection systems that may be added to the sensing system 100 and user interaction device 1010 to affect the feedback response provided to the user 1710.

Although FIGS. 10-17 illustrate user interaction with a plant, any living organism may be coupled to a sensing system where a change in the electrical signal propagating in the organism results in a feedback response. For example, the sensing system may be coupled to an animal where the particular user interactions with the animal may trigger different feedback responses.

CONCLUSION

Embodiments described herein use capacitive sensing to detect human interaction with living plants. Specifically, a sensing system may utilize the natural conductive paths found in an organic plant to transmit an electrical signal between the plant and the user interacting with the plant. The user may interact with the plant by either directly contacting the plant or affecting an electrical field emitted by the plant. That is, the electrical properties of the user (e.g., the capacitance of the human body) change a measured impedance curve associated with the electrical signal. Based on the change, the sensing system detects an interaction between the user and the plant. For example, touching the leaf of the plant may cause a different change in the impedance curve than touching the stem of the plant. The sensing system may be configured to detect these differences and provide this information to a user interaction device. The user interaction device may choose one or more feedback responses (e.g., audio or visual effects) to provide to the user based on the type of user interaction.

The flowchart and block diagrams in the Figures illustrate the architecture, functionality, and operation of possible implementations of systems, methods and computer program products according to various embodiments of the present invention. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order or out of order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

While the foregoing is directed to embodiments of the present invention, other and further embodiments of the invention may be devised without departing from the basic scope thereof, and the scope thereof is determined by the claims that follow.

What is claimed is:

1. A method, comprising:
   transmitting an alternating current (AC) signal at two different frequencies in an organic plant;
   measuring an impedance curve by scanning the AC signal through a frequency range comprising the two different frequencies;
   detecting a change in the impedance curve based on measuring impedance values at the two different frequencies, wherein the change in the impedance curve is caused by a subject becoming electrically coupled to the organic plant;
   correlating the impedance curve to one or more predefined impedance curves, each predefined impedance curve corresponding to a particular action performed by the subject;
   identifying an action performed by the subject based on the change in the impedance curve, wherein the particular action corresponding to the predefined impedance curve that correlates to the impedance curve is the identified action; and
   providing a feedback response to the subject based on the identified action.

2. The method of claim 1, wherein the impedance curve is changed by a reactance associated with the subject.

3. The method of claim 1, wherein the subject is electrically coupled to the organic plant by at least one of (i) directly contacting the organic plant and (ii) affecting, without physically contacting the plant, an electrical field emitted by the organic plant as a result of the AC signal.

4. The method of claim 1, further comprising, after providing the feedback response:
   detecting a different change in the impedance curve;
   identifying a different action performed by the subject based on the different changed of the impedance curve; and
   providing a different feedback response to the subject based on the different identified action.

5. The method of claim 1, wherein identifying the action performed by the subject comprises characterizing the performed action by at least one (i) physical contact with a specific, anatomic portion of the organic plant, (ii) the pressure applied when contacting the organic plant, (iii) a motion associated with the performed action, (iv) number of contact points (v) size of contact area and (vi) distance between the subject and the organic plant.

6. The method of claim 1, further comprising:
   identifying a secondary interaction between the subject and the organic plant using a supplemental sensing system, the supplemental sensing system identifies the secondary interaction without using the AC signal;
   selecting the feedback response based on the secondary interaction identified by the supplemental sensing system.

7. The method of claim 1, wherein the identified action defines a distance between the subject and the organic plant, wherein the subject does not contact the plant while performing the action, further comprising:
   selecting the feedback response based on the distance between the subject and the organic plant.

8. The method of claim 1, further comprising:
   receiving a returned AC signal;
   converting the returned AC signal to a time-varying direct current (DC) signal;
   determining a defined impedance parameter of the time-varying DC signal, where the defined impedance parameter defines an electromagnetic resonant attribute of the subject; and
   identifying the action performed by the subject based on the electromagnetic resonant attribute.

9. A method, comprising:
   transmitting a first AC signal at two different frequencies in a first organic plant;
   detecting a change in a parameter based on measuring impedance values at the two different frequencies, wherein the changed parameter is caused by a subject becoming electrically coupled to the first organic plant;
   identifying an action performed by the subject based on the changed parameter; and
   before providing a feedback response:
      determining, by transmitting a second AC signal, that a parameter in a second organic plant is changed by human interaction; and
      upon determining that both the parameter associated with the first organic plant and the parameter associated with the second organic plant are changed, providing the feedback response to the subject based on the identified action.

10. A system, comprising:
    an organic plant;
    a sensing component configured to:
       transmit an alternating current (AC) signal at two different frequencies in the organic plant,
       measure an impedance curve by scanning the AC signal through a frequency range comprising the two different frequencies,
       detect a change in the impedance curve based on measuring impedance values at the two different frequencies, wherein the change in the impedance curve is caused by a subject becoming electrically coupled to the organic plant, and
       correlate the impedance curve to one or more predefined impedance curves, each predefined impedance curve corresponding to a particular action performed by the subject,
    wherein the change in the impedance curve is used to identify an action performed by the subject, wherein the particular action corresponding to the predefined impedance curve that correlates to the impedance curve is the identified action; and
    a user interaction device communicatively coupled to the sensing component, the user interaction device configured to provide feedback response to the subject based on the identified action.

11. The system of claim 10, wherein the impedance curve is changed by a reactance associated with the subject.

12. The system of claim 10, wherein the sensing component is configured to:
    measure a plurality of impedance curves by repeatedly scanning the AC signal through the frequency range comprising the two different frequencies.

13. The system of claim 10, further comprising a supplemental sensing component configured to identify a secondary interaction between the subject and the organic plant without using the AC signal, wherein the feedback response is further based on the secondary interaction.

14. The system of claim 10, wherein the subject is electrically coupled to the organic plant by at least one of (1) directly contacting the organic plant and (2) affecting, without physically contacting the plant, an electrical field emitted by the organic plant as a result of the AC signal.

15. The system of claim 10, wherein the identified action defines a distance between the subject and the organic plant, wherein the subject does not contact the plant while performing the action, further comprising:
    selecting the feedback response based on the distance between the subject and the organic plant.

16. The system of claim 10, wherein the sensing component is configured to:
    receive a returned AC signal based on transmitting the AC signal;
    convert the returned AC signal to a time-varying direct current (DC) signal;
    determine a defined impedance parameter of the time-varying DC signal, where the defined impedance parameter defines an electromagnetic resonant attribute of the subject; and
    identify the action performed by the subject based on the electromagnetic resonant attribute.

17. A system, comprising:
a first organic plant;
a first sensing component configured to:
    transmit a first alternating current (AC) signal at two different frequencies in the first organic plant, and
    detect a change in a first parameter based on measuring impedance values at the two different frequencies, wherein the first parameter is caused by a subject becoming electrically coupled to the first organic plant,
wherein the first parameter is used to identify an action performed by the subject;
a user interaction device communicatively coupled to the first sensing component, the user interaction device configured to provide feedback response to the subject based on the identified action;
a second organic plant;
a second sensing component communicatively coupled to the user interaction device, the second sensing component transmits a second AC signal in the second organic plant, wherein the second sensing component is configured to, before providing the feedback response, determine that a second parameter associated with the second organic plant is changed by human interaction,
wherein the user interaction device is configured to provide the feedback response upon determining that both the first parameter associated with the first organic plant and the second parameter associated with the second organic plant are changed.

* * * * *